(12) United States Patent
Hüls et al.

(10) Patent No.: US 6,579,681 B1
(45) Date of Patent: Jun. 17, 2003

(54) TEST SYSTEM FOR DETECTING A SPLICING REACTION AND USE THEREOF

(75) Inventors: Christoph Hüls, Herne (DE); Bettina Bauer, Frankfurt (DE); Claus Simandi, Frankfurt (DE); Reinhard Lührmann, Marburg (DE); Tilmann Achsel, Göttingen (DE); Hans-Peter Vornlocher, Bayreūth (DE)

(73) Assignee: Aventis Research and Technologies GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/857,063

(22) PCT Filed: Feb. 25, 2000

(86) PCT No.: PCT/EP00/01595

§ 371 (c)(1),
(2), (4) Date: Nov. 27, 2001

(87) PCT Pub. No.: WO00/52201

PCT Pub. Date: Sep. 8, 2000

(30) Foreign Application Priority Data

Mar. 2, 1999 (DE) .......................... 199 09 156

(51) Int. Cl.[7] .......................... C12Q 1/68; C07H 21/04
(52) U.S. Cl. .......................... 435/6; 536/23.1
(58) Field of Search ...................... 435/6, 810; 536/23.1

(56) References Cited

U.S. PATENT DOCUMENTS 5,849,484 A * 12/1998 Leibowitz et al. ............. 435/6

FOREIGN PATENT DOCUMENTS

| WO | 95/076364 | 3/1995 |
|----|-----------|--------|
| WO | 97/15679 | 5/1997 |
| WO | 98/08381 | 3/1998 |

OTHER PUBLICATIONS

Jenison, R. D., et al, "High–Resolution Molecular Discrimination by RNA," *Science 263:*1425–1429, XP–000567866 (1994).

Morgan, W. R., et al, "Three Splicing Patterns Are Use To Excise the Small Intron Common to all Minute Virus of Mice RNAs," *J. of Virology 60:*1170–1174, XP–000961665 (1986).

Sawa, H., et al, "Alterations of RNase H sensitivity of the 3' splice site region during the in vitro splicing reaction," *Nuc;eoc Acids Research 19:*3953–3958, XP–002155141 (1991).

Wang, Y., et al, "RNA Molecules That Specifically and Stoichiometrically Bind Aminoglycoside Antibiotics with High Affinities," *Biochemistry 35:*12338–12346, XP–002155142 (1996).

Utans, U., et al, "Splicing factor SF4 is dispensable for the assembly of a functional splicing complex and participates in the subsequent step . . . ,"*The EMBO Journal 9:*4119–4126, XP–002155143 (1990).

Mougin, A., et al, "Secondary structure of the yeast *Saccharomyces cerevisiae* pre–U3A snoRNA and its implication for splicing efficiency," *RNA 2:*1079–1093, XP–002155144 (1996).

Hughes, J.M.X., et al, "The yeast homologue of U3 snRNA," *The EMBO Journal 6:*2145–2155, XP–002155146 (1987).

Konarska, M. M., et al, "Characterization of the branch site in lariat RNAs produced by splicing of mRNA precursors," *Nature 313:*552–557 & Database EMBL 'Online!', XP–002155147 (1994).

* cited by examiner

Primary Examiner—Kenneth R. Horlick
(74) Attorney, Agent, or Firm—Connolly Bove Lodge & Hutz LLP

(57) ABSTRACT

The present invention relates to a test system comprising
(a) one or more identical or different immobilized nucleic acid(s) having at least one spliceable nucleic acid,
(b) at least one gel-free detection system for detecting a splicing reaction, where appropriate
(c) at least one composition comprising splicing components, and preferably
(d) suitable detection probes, and, where appropriate,
(e) further aids.

32 Claims, 12 Drawing Sheets

Fig. 1A taatacgactcactataGGGCGAATTCGAGCTCGCCCACTCTTGGATCGGAAACCCGTCGGCCTCC
        ---T7 Promoter--------.........Exon1............

GAACGgtaagagcctagcatgtagaactggttacctgcagcccaagcttgctgcacgtctagggcg
.....---------------------------------Intron------------------------ cagtagtccagggtttccttgatgatgtcatacttatcctgtccctttttttttccacagCTCGCGG
----------------------------------Intron---------------------.Exon2

TTGAGGACAAACTCTTCGCGGTCTTTCCAGTGGGGATCCAAGTGATACCAGCATCGTCTTGATGCC
................Exon 2.............========Aptamer Th==========

CTTGGCAGCACTTGGATCC
==Aptamer Th======

Fig. 1B ttaatacgactcactataGGGCGAATTCGAGCTCGCCCACTCTTGGATCGGAAACCCGTCGGCCTC
         ---T7 Promoter-----.......Exon 1................

CGAACGgtaagagcctagcatgtagaactggttacctgcagcccaagcttgctgcacgtctagggc
......--------------------------------Intron---------------------- gcagtagtccagggtttccttgatgatgtcatacttatcctgtccctttttttttccacagCTCGCG
--------------------------------Intron--------------------.Exon2

GTTGAGGACAAACTCTTCGCGGTCTTTCCAGTGGGGATCGGCTTAGTATAGCGAGGTTTAGCTACA
.................Exon 2.............=======Aptamer To==========

CTCGTGCTGAGCCGGATCC
===Aptamer To=====

Fig. 2A taatacgactcactataGGGCGAATTCGAGCTCGCCCACTCTTGGATCGGAAACCCGTCGGCCTCC
................---T7 Promoter-----........Exon 1................

GAACGgtaagagcctagcatgtagaactggttacctgcaAAGTGATACCAGCATCGTCTTGATGCC
......-----------Intron--------------------=======Aptamer Th=========

CTTGGCAGCACTTCTGCAgcccaagcttgctgcacgtctagggcgcagtagtccagggtttccttg
==Aptamer Th======-------------------Intron------------------------ atgatgtcatacttatcctgtcccttttttttccacagCTCGCGGTTGAGGACAAACTCTTCGCGG
-----------Intron--------------------.........Exon2................

TCTTTCCAGTGGGGATCC
....Exon 2........

Fig. 2B taatacgactcactataGGGCGAATTCGAGCTCGCCCACTCTTGGATCGGAAACCCGTCGGCCTCC
................---T7 Promoter----........Exon1................

GAACGgtaagagcctagcatgtagaactggttacctgcaGGCTTAGTATAGCGAGGTTTAGCTACA
......-----------Intron------------------======Aptamer To=========

CTCGTGCTGAGCCCTGCAgcccaagcttgctgcacgtctagggcgcagtagtccagggtttccttg
==Aptamer To======------------------Intron------------------------ atgatgtcatacttatcctgtccctttttttttccacagCTCGCGGTTGAGGACAAACTCTTCGCGG
-----------Intron--------------------..........Exon 2............

TCTTTCCAGTGGGGATCC
....Exon 2........

Fig. 3A

```
taatacgactcactataGGGCGAATTAAGTGATACCAGCATCGTCTTGATGCCCTTGGCAGCACTT
...............---T7----============Aptamer Th=================
                 Promoter GAATTCGAGCTCGCCCACTCTTGGATCGGAAACCCGTCGGCCTCCGAACGgtaagagcctagcatg
=====..............Exon 1.......................------Intron---- tagaactggttacctgcagcccaagcttgctgcacgtctagggcgcagtagtccagggtttccttg
---------------------------Intron-------------------------------- atgatgtcatacttatcctgtccctttttttttccacagCTCGCGGTTGAGGACAAACTCTTCGCGG
---------------Intron-----------------...........Exon 2..........

TCTTTCCAGTGGGGATCC
....Exon 2.......
```

Fig. 3B

```
taatacgactcactataGGGCGAATTGGCTTAGTATAGCGAGGTTTAGCTACACTCGTGCTGAGCC
.................---T7----============Aptamer To=================
                Promoter GAATTCGAGCTCGCCCACTCTTGGATCGGAAACCCGTCGGCCTCCGAACGgtaagagcctagcatg
=====.............Exon 1......................------Intron---- tagaactggttacctgcagcccaagcttgctgcacgtctagggcgcagtagtccagggtttccttg
--------------------------Intron-------------------------------- atgatgtcatacttatcctgtccctttttttttccacagCTCGCGGTTGAGGACAAACTCTTCGCGG
---------------Intron----------------...........Exon 2.........

TCTTTCCAGTGGGGATCC
....Exon 2......
```

Fig. 4A

TAATACGACTCACTATAGGGCGAATTGGAGCTCCACCGC(Th/To)CCGCGGTGGCGGCCGCTCTA
         ---T7 Promoter--------/          /----------------
                                        Aptamer
                                        insertion site GAACTAGTGGATCCGTCGACTGACTTCAgtatgtaatataccccaaacattttacccacaaaaaac
--------------...Exon 1.....---------------Intron------------------ caggatttgaaactatagcatctaaaagtcttaggtactagagttttcatttcggagcaggctttt
----------------------------Intron-------------------------------- tgaaaaatttaattcaaccattgcagcagcttttgactaacacattctacagTAGGATCATTTCTA
---------------------------Intron------------------.....Exon 2...

TAGGAATCGTCACTCTTTGACTCTTCAAAAGAGCCACTGAATCCAACTTGGTTGATGAGTCCCATA
.......................Exon 2....................................

ACCTTTGTACCCCAGAGTGAGAAACCGAAATTGAATCTAAATTAGCTTGGTCCGCAATCCTTAGCG
.........................Exon 2..................................

TTCGGCCATCTATAATTTTGAATAAAAATTTTGCTTTGCCGTTGCATTTGTAGTTTTTTCCTTTGG
.........................Exon 2..................................

AAGTAATTACAATATTTTATGGCGCGATGATTCTTGACCCATCCTATGTACTTCTTTTTTTGAAGGG
.........................Exon 2..................................

ATAGGGCTCTATGGGTGGGTACAAATGGCAGTCTGACAAGTT
..........................................

Fig. 4B

```
TAATACGACTCACTATAGGGCGAATTGGAGCTCCACCGCGGTGGCGGCCGCTCTAGAACTAGTGGA
               ---T7 Promoter-------------------------------

TCCGTCGACTGACTTCAgtatgtaatataccccaaacatttTacccacaaaaaaacca(Th/To)CC
---...Exon 1.....---------------Intron--------------------/
                                                          Aptamer
                                                     insertion site Aggatttgaaactatagcatctaaaagtcttaggtactagagttttcatttcggagcaggcttttt
/-------------------------------Intron---------------------------- gaaaaatttaattcaaccattgcagcagcttttgactaacacattctacagTAGGATCATTTCTAT
-------------------------------Intron--------------.....Exon 2....

AGGAATCGTCACTCTTTGACTCTTCAAAAGAGCCACTGAATCCAACTTGGTTGATGAGTCCCATAA
........................Exon 2............................

CCTTTGTACCCCAGAGTGAGAAACCGAAATTGAATCTAAATTAGCTTGGTCCGCAATCCTTAGCGT
........................Exon 2............................

TCGGCCATCTATAATTTTGAATAAAAATTTTGCTTTGCCGTTGCATTTGTAGTTTTTTCCTTTGGA
........................Exon 2............................

AGTAATTACAATATTTTATGGCGCGATGATTCTTGACCCATCCTATGTACTTCTTTTTTGAAGGGA
........................Exon 2............................

TAGGGCTCTATGGGTGGGTACAAATGGCAGTCTGACAAGTT
........................Exon 2....
```

Fig. 4C

```
TAATACGACTCACTATAGGGCGAATTGGAGCTCCACCGCGGTGGCGGCCGCTCTAGAACTAGTGGA
              ---T7 Promoter-------------------------------

TCCGTCGACTGACTTCAgtatgtaatataccccaaacatttttacccacaaaaaaccaggatttgaa
---...Exon 1.....--------------Intron----------------------------- actatagcatctaaaagtcttaggtactagagttttcatttcggagcaggcttttttgaaaaattta
--------------------------------Intron---------------------------- attcaaccattgcagcagcttttgactaacacattctacagTAGGATCATTTCTATAGGAATCGTC
------------------------------Intron-----.........Exon 2..........

ACTCTTTGACTCTTCAAAAGAGCCACTGAATCCAACTTGGTTGATGAGTCCCATAACCTTTGTACC
.................................Exon 2.........................

CCAGAGTGAGAAACCGAAATTGAATCTAAATTAGCTTGGTCCGCAATCCTTAGCGTTCGGCCATCT
................................Exon 2..........................

ATAATTTTGAATAAAAATTTTGCTTTGCCGTTGCATTTGTAGTTTTTTCCTTTGGAAGTAATTACA
................................Exon 2..........................

ATATTTTATGGCGCGATGATTCTTGACCCATCCTATGTACTTCTTTTTTGAAGGGATAGGGCTCTA
................................Exon 2..........................

TGGGTGGGTACAAATGGCAGTCTGACAAGTT(Th/Tc)
.........Exon 2.............../Aptamer insertion site
```

Fig. 5A taatacgactcactataGGGCGAATTCGAGCTCGCCCACTCTTGGATCGGAAACCCGTCGGCCTCC
................---T7-Promoter-----............Exon 1............

GAACGgtaagagcctagcatgtagaactggttacctgcagcccaagcttgctgcacgtctagggcg
......------------------------Intron------------------------------ cagtagtccagggtttccttgatgatgtcatacttatcctgtcccttttttttccacagCTCGCGG
------------------------Intron------------------------.Exon 2

TTGAGGACAAACTCTTCGCGGTCTTTCCAGTGGGGATCGGGGATCCTGCTTCAACAGTGCTTGGAC
.......Exon 2.........................==========IRE===============

GGATCCTCTAGAC
===IRE======

Fig. 5B

```
TAATACGACTCACTATAGGGCGAATTGGAGCTCCACCGCGGTGGCGGCCGCTCTAGAACTAGTGGA
                    -------------------T7-Promoter------------------

TCCGTCGACTGACTTCAgtatgtaatataccccaaacatttttacccacaaaaaaccaggatttgaa
..Exon 1......----------------Intron---------------------------- actatagcatctaaaagtcttaggtactagagttttcatttcggagcaggcttttgaaaaattta
--------------------------------Intron--------------------------- attcaaccattgcagcagcttttgactaacacattctacagTAGGATCATTTCTATAGGAATCGTC
-------------------Intron-----------------.........Exon 2.........

ACTCTTTGACTCTTCAAAAGAGCCACTGAATCCAACTTGGTTGATGAGTCCCATAACCTTTGTACC
.......................Exon 2...................................

CCAGAGTGAGAAACCGAAATTGAATCTAAATTAGCTTGGTCCGCAATCCTTAGCGTTCGGCCATCT
.......................Exon 2...................................

ATAATTTTGAATAAAAATTTTGCTTTGCCGTTGCATTTGTAGTTTTTTCCTTTGGAAGTAATTACA
.......................Exon 2...................................

ATATTTTATGGCGCGATGATTCTTGACCCATCCTATGTACTTCTTTTTTGAAGGGATAGGGCTCTA
.......................Exon 2...................................

TGGGTGGGTACAAATGGCAGTCTGACAAGTTGGGGATCCTGCTTCAACAGTGCTTGGACGGATCCT
..........Exon 2...................==============IRE==============

CTAGAC
=IRE=
```

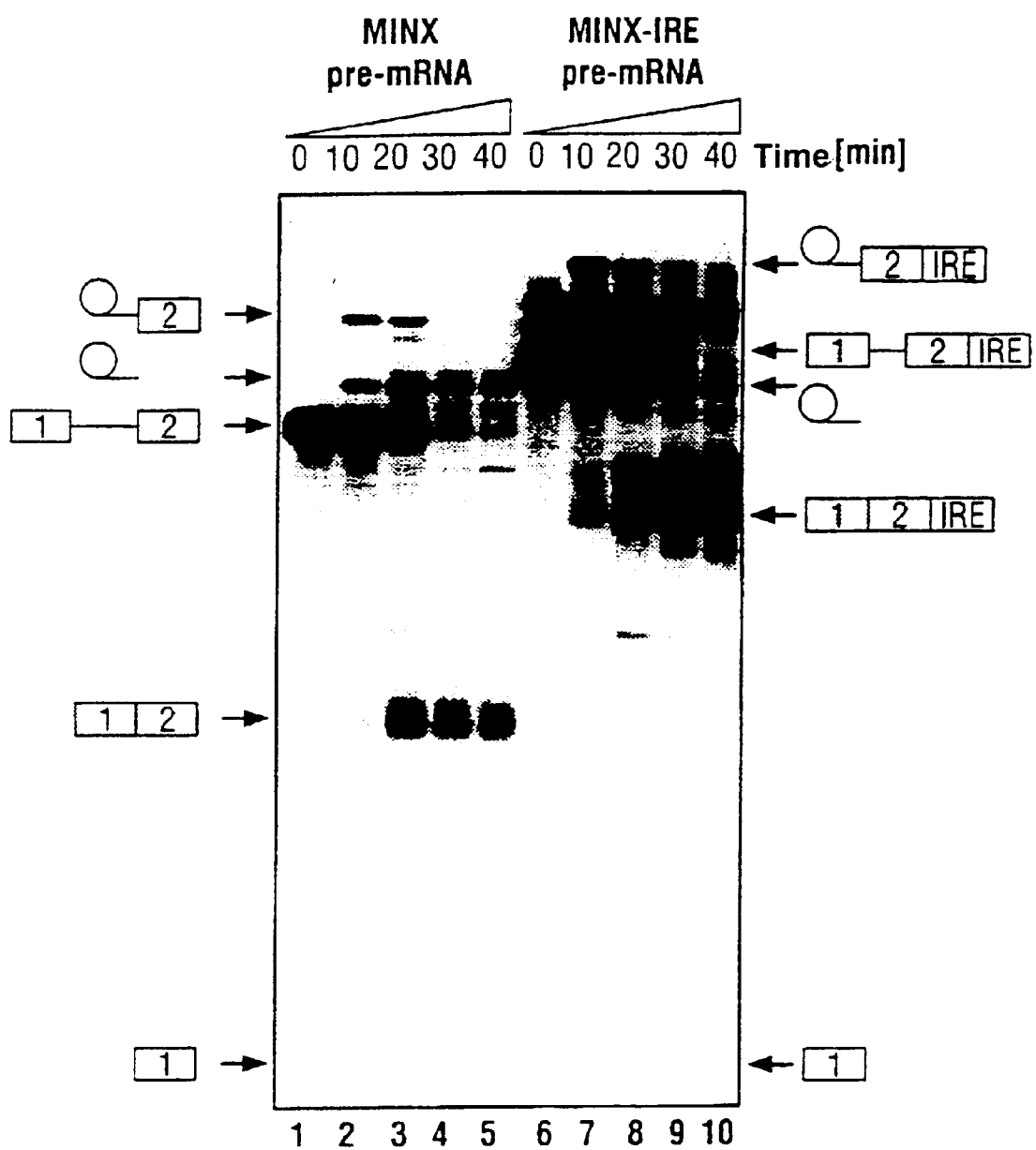

TEST SYSTEM FOR DETECTING A SPLICING REACTION AND USE THEREOF

DESCRIPTION

The present invention relates to a test system comprising (a) one or more identical or different immobilized nucleic acid(s) having at least one spliceable nucleic acid.

(b) at least one gel-free detection system for detecting a splicing reaction, where appropriate (c) at least one composition comprising splicing components, and preferably (d) suitable detection probes, and, where appropriate, (e) further aids.

Most of the protein-encoding genes in eukaryotes are interrupted in their genomic form by one or more sequences not coding for the protein (introns). When transcribing the genomic DNA into messenger RNA (mRNA), these non-coding regions (introns) are incorporated into the primary transcript. In order to generate the correct mRNA, this pre-mRNA has to be processed.

The pre-mRNA is processed by removing the introns and fusion of the coding regions (exons). Only then is it possible to provide a nucleotide strand which can be read in an interrupted manner for translation in the cytoplasm. mRNA formation in eukaryotes therefore requires a "splicing process" in which the non-coding gene regions (introns) are removed from the primary gene transcript.

Splicing occurs in the nucleus, before the mRNA is transported out of the nucleus. It is generally carried out in a two-stage mechanism in which in each case a transesterification step is involved (Moore, J. M. et al., (1993) Splicing of precursors to mesenger RNAs by the Spliceosome. In The RNA world, Edited by Gesteland R. F., Gesteland, J. F., Cold Spring Harbor Laboratory Press, 303–358). The first step generates a free 5' exon and a "lariat structure" of the intron which is still linked to the 3' exon. The lariat structure comprises a branched RNA which is produced by esterification of the 5' end of the intron with a 2'-hydroxyl group of a ribose in an adenosine which is located approx. 20–40 nucleotides upstream of the 3' end of the intron. The second catalytic step leads to ligation of the exons and liberation of the intron. Although no nucleotides are incorporated during these reactions, an energy source, for example ATP, is necessary for this catalysis (Guthrie, C. (1991) Science, 253, 157).

A plurality of factors is involved in the process of mRNA splicing. Two classes of splicing factors are distinguished at the moment. The first class comprises four evolutionarily highly conserved protein-RNA particles (small nuclear ribonucleoprotein particles=snRNPs); U1, U2, U4/U6 and U5, which comprise either one (U1, U2, U5) or two (U4/U6) snRNA components (Moore, J. M. et al., (1993) supra; Guthrie, (1991) supra; Green, M. R. (1991), Annu. Rev. Cell Biol., 7, 559). The second class comprises proteins which have not been characterized much up until now and which are not tightly bound to the snRNPs and are therefore called non-snRNP splicing factors (Lamm, G. M. & Lamond, A. J. (1993) Biochim. Biophys. Acta, 1173, 247; Beggs, J. D. (1995), Yeast splicing factors and genetic strategies for their analysis, In: Lamond, A. I. (ed) Pre-mRNA Processing Landes, R.G. Company, Texas, pp. 79–95. Kämer A. (1995), The biochemistry of pre-mRNA splicing. In: Lamond, A. I. (ed), Pre-mRNA Processing. Landes, R.G. Company, Texas, pp. 35–64).

The composition of snRNPs has been studied most successfully in HeLa cells (Will, C. L. et al., (1995) Nuclear pre-mRNA splicing. In: Eckstein, F. and Lilley, D. M. J. (eds). Nucleic Acids and Molecular Biology. Springer Verlag, Berlin, pp. 342–372). At relatively low salt concentrations at which it is possible for nuclear extracts from HeLa cells to promote splicing of pre-mRNA in vitro, the snRNPs are present in a 12S U1 snRNP, a 17S U2 snRNP and a 25S [U4/U6.U5] tri-snRNP complex. At higher salt concentrations (approx. 350–450 mM) the tri-snRNP complex dissociates into a 20S U5 particle and a 12S U4/U6 particle. In the U4/U6 snRNP, the U4 and U6 RNAs are present base-paired via two intermolecular helices (Bringmann, P. et al. (1984) EMBO J., 3, 1357; Hashimoto, C. & Steitz, J. A. (1984) Nucleic Acids Res., 12, 3283; Rinke, J. et al., (1985) J. Mol. Biol., 185, 721; Brow. D. A. & Guthrie, C. (1988) Nature, 334, 213).

The snRNPs comprise two groups of proteins. All snRNPs comprise the group of general proteins (B/B', D1, D2, D3, E, F and G). In addition, each snRNP comprises specific proteins which are present only in said snRNP.

Thus, according to the prior state of research, U1 snRNP comprises three additional proteins (70K, A and C) and U2 snRNP eleven further proteins. According to prior knowledge, 20S U5 snRNP carries nine further proteins having molecular weights of 15, 40, 52, 100, 102, 110, 116, 200 and 220 kDa, while 12S U4/U6 snRNP comprises two additional proteins having molecular weights of approx. 60 and 90 kDa. 25S tri-snRNP [U4/U6.U5] comprises five additional proteins having molecular weights of approx. 15.5, 20, 27, 61 and 63 kDa (Behrens, S. E. & Lührmann, R. (1991) Genes Dev., 5, 1439; Utans, U. et al., (1992) Genes Dev., 6, 631; Lauber, J. et al., (1996) EMBO J., 15, 4001; Will, C. L. et al. (1995), supra, Will, C. L. & Lührmann, R. (1997) Curr. Opin. Cell Biol., 9, 320–328).

The composition of splicing components in *Saccharomyces cerevisiae* has not yet been studied in detail. Biochemical and genetic studies, however, indicate that the sequences of both the snRNAs and the snRNP proteins are evolutionarily highly conserved (Fabrizio, P. et al., (1994) Science, 264, 261; Lauber, J. et al., (1996), supra, Neubauer, G. et al., (1997) Proc. Natl. Acad. Sci. USA, 94, 385; Krämer, A. (1995), supra; Beggs, J. D. (1995); supra, Gottschalk, A. et al. (1998) RNA, 4, 374–393).

In order to form a functional splicing complex (spliceosome), the individual components (pre-mRNA, snRNPs and non-snRNP proteins) are combined in a stage-wise process. This is achieved not only by interactions of the pre-mRNA with the protein-containing components but also by numerous interactions between the protein-containing components themselves (Moore, J. M. (1993) supra; Madhani, H. D. & Guthrie, C. (1994) Annu. Rev. Genetics, 28, 1; Nilsen, T. W. (1994) Cell, 65, 115). The pre-mRNA sequence carries specific recognition sequences for the different splicing components. Firstly, U1 snRNP binds via said recognition sequences to the 5' splicing region of the pre-mRNA intron. At the same time, an as yet unspecified number of various other factors (e.g. SF2/ASF, U2AF, SC35, SF1) is taken up by this complex and cooperates with the snRNAs in the continued formation of the pre-spliceosome. The U2 snRNP particle interacts with the "branch site" in the intron region (Krämer, A. & Utans, U. (1991) EMBO J., 10, 1503; Fu, X. D. & Maniatis, T. (1992) Proc. Natl. Acad. Sci USA, 89, 1725; Krämer, A. (1992) Mol. Cell Biol., 12, 4545; Zamore, P. D. et al. (1992) Nature, 355, 609; Eperon, J. C. et al. (1993) EMBO J., 12, 3607; Zuo, P. (1994) Proc. Natl. Acad. Sci. USA, 91, 3363; Hodges, P. E. & Beggs, J. D. (1994) Curr. Biol. 4, 264; Reed, R. (1996) Curr. Op. Gen. Dev., 6, 215). In a last step of spliceosome formation, [U4/U6.U5] tri-snRNP and a number of proteins not yet characterized in detail interact with the pre-spliceosome, in order to form the mature spliceosome (Moore, J. M. et al., (1993) supra).

For the splicing process, various interactions between pre-mRNA, snRNAs and sn-RNP are removed and new ones are formed. Thus it is known that before or during the first catalytic step of the splicing reaction two helices are separated from one another in the interacting structures of U4 and U6 and that new interactions form base pairs between U2 RNAs and U6 RNAs (Datta, B. & Weiner, A. M. (1991) Nature, 352, 821; Wu, J. A. & Manley, J. L. (1991) Nature, 352, 818; Madhani, H. D. & Guthrie, C. (1992) Cell, 71, 803; Sun, J. S. & Manley, J. L. (1995) Genes Dev., 9, 843). At the same time, binding of U1 to the 5' splicing site is removed and pre-mRNA binds to the recognition sequence ACAGAG of U6 snRNA (Fabrizio, P. & Abelson, J. (1990), Science, 250, 404; Sawa, H. & Abelson, J. (1992) Proc. Natl. Acad. Sci. USA, 89, 11269; Kandels-Lewis, S, & Séraphin, B. (1993) Science, 262, 2035; Lesser, C. F. & Guthrie C. (1993) Science, 262, 1982; Sontheimer, E. J. & Steitz, J. A. (1993) Science, 262, 1989). U5 snRNP interacts via its conserved loop 1 with exon sequences which are located close to the 5' and 3' splicing sites. This process seems to be sequential, while the entire splicing process progresses from stage 1 to stage 2 (M. McKeown (1992) Annu. Rev. Cell Dev. Biol., 8: 133–155 Newman, A. & Norman, C. (1991) Cell, 65, 115; Wyatt, J. R. et al. (1992) Genes Dev., 6, 2542; Cortes, J. J. et al. (1993) EMBO J., 12, 5181; Sontheimer, E. J. & Steits (1993) supra). After the splicing reaction has finished, the mature mRNA is liberated and the spliceosome dissociates (Moore, J. M. et al (1993) supra).

Alternative splicing makes it possible to form from one and the same primary transcript various mature mRNAs which code for various proteins. In many cases, this alternative splicing is regulated. Thus it is possible to utilize this mechanism, for example, for the purpose of switching from a non-functional to a functional protein (e.g. transposase in Drosophila). It is furthermore known that alternative splicing is carried out tissue-specifically. Thus, for example, tyrosine kinase which is encoded by the src proto-oncogene is synthesized in nerve cells in a specific form by alternative splicing.

Incorrectly regulated or performed alternative splicing may lead to various conditions. In patients suffering from Graves' disease it has been shown that incorrect splicing produces a crucial enzyme (thyroperoxidase) in an inactive form (Zanelli, E. (1990) Biochem. Biophys. Res. Comm., 170, 725). Studies of the disease spinal muscular atrophy indicate that a defective gene product of the SMN (survival of motor neurons) gene leads to a considerable disruption in the formation of snRNPs. Inhibition of the splicing apparatus of the motor neurons leads to paralysis of the nerve cells and to degeneration of muscle tissue (Fischer, U. et al. (1997), Cell, 90: 1023–9; Liu, Q. et al. (1997), Cell, 90: 1013–21; Lefebvre, S. et al. (1997) Nat. Genet. 16, 265). Particular alternative splicing variants of the membrane-bound molecule CD44, inter alia, seem to play a decisive part in cancer cell metastasis. The CD44 gene comprises a plurality of exons, 10 exons of which, located next to one another, are spliced from the pre-mRNA in different arrangement during mRNA generation. In rat carcinoma cells it was detected that metastasizing variants carry exons 4 to 7 or 6 to 7. With the aid of antibodies against the exon 6-encoded part of the protein it was possible to suppress metastasis efficiently (Sherman, L., et al. (1996) Curr. Top. Microbiol. Immunol. 213: 249–269).

Incorrect splicing may lead to strongly developed phenotypes of the affected organism. Thus it is known that a point mutation in a β-globin intron may lead to a $β^+$ thalassemia. The point mutation produces an incorrect splicing location which leads to a modified reading frame and to preliminary termination of the peptide chain (Weatherall, D. J. & Clegg, J. B. (1982) Cell, 29, 7; Fukumaki, Y. et al. (1982) Cell, 28, 585). In *Arabidopsis thaliana* mutants, for example, a point mutation at the 5' splicing site of the phytochrome B gene leads to incorrect expression of the gene. This modification makes it impossible to remove an intron whose sequence includes a stop codon. Development of the plants is disrupted, since the gene is involved in phytomorphogenesis (Bradley, J. M. et al. (1995) Plant Mol. Biol., 27, 1133).

Up until now, only a few studies have been known, which have described influencing of splicing processes in the cell. Thus it is possible, with the aid of antisera or monoclonal antibodies against components of the splicing apparatus, to prevent generation of mature mRNA (Padgett, R. A. et al. (1983) Cell, 35, 10; Gattoni, R. et al. (1996) Nucleic Acid Res., 24, 2535).

The NS1 protein which is encoded by the influenza virus genome may likewise interfere in splicing by binding to U6 snRNA. The protein binds to nucleotides 27–46 and 83–101 of human U6 snRNA and thus prevents U6 from being able to interact with the partners U2 and U4 during the splicing process (Fortes, P. et al. (1994) EMBO J., 13, 704; Qiu, Y. & Krug, R. M. (1995) J. Virol., 68, 2425). Moreover, the NS1 protein also seems to prevent export from the nucleus by binding to the polyA tail of the mRNA formed (Fortes, P. et al. (1994), supra; Qiu, Y. & Krug, R. M. (1994), supra). Similar actions are described for a gene product of the Herpes simplex virus type 1 genome. In in vitro experiments, the protein ICP27 was able to effectively prevent splicing of a model RNA (β-globin pre-mRNA) (Hardy, W. R. & Sandri-Goldin, R. M. (1994) J. Virol., 68, 7790). In addition, peptides which have been generated from the C-terminal domain of the large subunit of RNA polymerase II seem likewise to be able to interfere in splicing processes (Yurvey, A. et al. (1996) Proc. Natl. Acad. Sci USA, 93, 6975; WO97/20031). The incorporation of artificial nucleotide analogs (5-fluoro-, 5-chloro- or 5-bromouridine) into the mRNA to be spliced may likewise lead to inhibition of the splicing process in vitro (Sierakowska, H. et al. (1989) J. Biol. Chem., 264, 19185; Wu, X. P. & Dolnick, B. (1993) Mol. Pharmacol., 44, 22).

A number of further studies relates to the action of antisense oligo-nucleotides on splicing. Thus, the ratio of two different splicing products of the c-erb oncogene mRNA (c-erbA-alpha 1 and 2) from rats seems to be regulated by another mRNA, rev-ErbA-alpha. Rev-ErbA-alpha is a naturally occurring antisense RNA which pairs with c-erbA-alpha 2 mRNA but not with c-erbA-alpha 1 mRNA. An excess of rev-ErbA-alpha mRNa constructs which were complementary to the 3' splicing site made it possible to effectively inhibit splicing of c-erbA-alpha pre-mRNA to c-erbA-alpha 2 mRNA (Munroe, S. H. & Lazar, M. A. (1991) J. Biol. Chem. 266 (33), 22083). Furthermore it was shown that generation of antisense RNA which bind to intron sequences of the mRNA to be spliced may likewise inhibit splicing (Volloch, V. et al. (1991) Biochem. Biophys. Res. Comm., 179, 1600). Hodges and Crooke were able to show that for weakly recognized splicing sites oligonucleotide binding is sufficient in order successfully to stop splicing. If, however, preferably recognized splicing sites are incorporated into the constructs, oligonucleotides which in addition can cause activation of RNase H are required (Hodges, D. & Crooke S. T. (1995) Mol. Pharmacol., 48, 905). A more detailed analysis of the pre-mRNA sequences required for splicing showed that 19 nucleotides upstream from the branching point adenosine and 25 nucleotides around the 3' and 5' splicing site are suitable sequences for generating antisense RNAs (Dominski, Z. & Kole, R. (1994) Mol. Cell Biol., 14, 7445). Studies with antisense molecules were carried out in particular for inhibition of viruses. Viruses which effect higher organisms often carry intron-containing genes in their genome. Thus it was possible to show that antisense oligo-nucleotides against the 3' splicing site of the immediate early pre-mRNA 4/5 gene of Herpes simplex virus was able to inhibit virus replication in Vero cells (Iwatani, W. et al. (1996) Drug Delivery Syst., 11, 427).

The splicing mechanism is studied in general firstly by preparing mRNA by in vitro transcription. To this end, genetic constructs from viruses, for example adenoviruses, or cellular structural genes are used. mRNAs of this kind include all important structural elements which are necessary for recognition of the mRNA by the spliceosome and for the splicing process. Generally, the mRNA is radiolabelled in order to make it possible, after fractionation on a denaturing urea polyacrylamide gel, to evaluate, owing to the characteristic band pattern, whether a splicing reaction has occurred or in which reaction step a disruption has occurred. However, test systems of this kind are very time-consuming and labor-intensive and are therefore not suited to the systematic finding of substances which can modulate splicing.

It was therefore an object of the present invention to find a test system which makes it possible to study in a simple and effective manner a large number of compounds from chemical or natural substance libraries for their action on splicing of nucleic acids (high throughput screening).

Surprisingly, it has now been found that a test system with a gel-free detection system for detecting a splicing reaction is suitable to overcome the above-described disadvantages of the conventional test system and is thus suitable for high throughput screening, for example in a robot system.

The present invention therefore relates to a test system comprising (a) one or more identical or different immobilized nucleic acid(s) having at least one spliceable nucleic acid.

(b) at least one gel-free detection system for detecting a splicing reaction, where appropriate (c) at least one composition comprising splicing components, and preferably (d) suitable detection probes, and, where appropriate, (e) further aids.

To provide a gel-free test system for studying splicing processes, the nucleic acid to be studied has to be immobilized to a solid phase. The nucleic acid may be immobilized, for example, covalently, by introducing particular structural elements, for example aptamers, into the nucleic acid to be spliced and using binding partners for said structural elements or by hybridization.

Additionally and advantageously, a suitable probe which facilitates detection of the splicing which has or has not occurred has to be generated for the gel-free test system. Said probe may be, for example, an oligonucleotide used for hybridization to the nucleic acid to be studied or a binding partner which binds to structural elements introduced into the nucleic acid to be studied.

Therefore, the gel-free detection system advantageously comprises at least one probe. The probe is in particular a nucleic acid complementary to the spliceable nucleic acid, a low molecular weight compound which binds the spliceable nucleic acid, and/or a peptide or protein which binds the spliceable nucleic acid.

In a preferred embodiment the spliceable nucleic acid comprises at least two exons which are separated by at least one intron.

For example, the complementary nucleic acid is complementary to at least one intron, to at least one exon and/or to at least one exon/intron transition site and/or to the exon/exon boundary generated after fusion of the two exons. The complementary nucleic acid here serves as a probe for detecting a splicing reaction.

Thus it is possible, for example, to detect the intron liberated during the splicing reaction by means of the gel-free detection system, and this leads to the conclusion that both steps of the splicing reaction have been completed. Alternatively, it is possible to determine on the basis of a suitable detection system, for example a nucleic acid complementary to an exon/intron transition site, whether the exon has been removed from the intron during the splicing process; this may provide information about whether the first splicing reaction has taken place at the 5' end of the intron and/or the second splicing reaction at the 3' end of the intron. Other forms of detection are illustrated in detail hereinbelow.

In a particularly preferred embodiment, the probe is a low molecular weight compound, for example theophylline, xanthine or an aminoglycoside such as tobramycin. If, for example, the spliceable nucleic acid or a nucleic acid of the gel-free detection system, which is complementary to the spliceable nucleic acid, comprises an "aptamer structure", i.e. a binding sequence for this kind of binding partner (see, for example, Jenison, R. D. et al (1994) Science 263, 1425–1429, Hamasaki, K. et al. (1998) Biochem. 37, 656–663 or Kiga, D. et al. (1998) Nucleic Acids Res., 26 (7), 1755–1760), then the splicing process can be detected particularly easily via the binding partner.

In another particularly preferred embodiment, the binding partner may be a nucleic acid binding protein, in particular an iron responsive element binding protein (IBP), which recognizes a recognition sequence for a nucleic acid binding protein, in particular an iron responsive element (IRE). A splicing process which may have occurred is detected here via the nucleic acid binding protein.

The described interactions between binding partner and structural element in the nucleic acid (low molecular weight compound and aptamer, IBP and IRE, oligonucleotide and sequence in the nucleic acid) are likewise suitable for immobilizing the nucleic acid to be studied and capable of being spliced to a solid phase. To this end, the binding partner must be anchored to the solid phase in a suitable manner. In this connection it is possible, for example, to bind the binding partner covalently to the solid phase. Furthermore, coupling of biotin to the nucleic acid and the use of (strept)avidin bound to the solid phase are suitable for anchoring the nucleic acid. Said anchoring may also be achieved, for example, by using antibody/antigen interactions.

Generally, the probe comprises a label, for example a radiolabel, a label by fluorescent dyes, by biotin, by digoxigenin and/or by antibodies. The label is preferably attached to the ligand, for example to the complementary nucleic acid, to the low molecular weight compound or to the nucleic acid binding protein. It is possible, in particular with the aid of fluorescent dyes, to determine in a simple and, in automated systems, rapid manner, whether it is possible for a splicing reaction to progress undisturbed, for example in the presence of at least one substance to be studied, for example by removing the binding partner of the probe in the nucleic acid during the splicing process.

In another preferred embodiment, the spliceable nucleic acid and the probe-binding nucleic acid are linked to one another. This has the advantage of it being possible to detect the splicing reaction directly, for example via liberation of the probe-binding nucleic acid. In this embodiment, the probe-binding nucleic acid is preferably a nucleic acid which can bind a low molecular weight compound, for example an "aptamer", and/or a nucleic acid binding protein. Since, generally, particular structural elements of the nucleic acids are responsible for binding of probes of this kind, the probe-binding nucleic acid is abbreviated in the preferred constructs below to "SE" for structural element, where "3' region" is a nucleic acid section at the 3' end of the nucleic acid:

1. Constructs with a structural element (SE) introduced into the 5' exon:
   ---T7 promoter---SE---exon1---intron---exon2---3'region---
   ---T7 promoter---exon1---SE---exon1---intron---exon2---3'region---
2. Construct with a structural element introduced into the intron:
   ---T7 promoter---exon 1---intron---SE---intron---exon2---3'region---
3. Constructs with a structural element introduced into the 3' exon:
   ---T7 promoter---exon1---intron---exon2---SE---exon2---3'region---
   ---T7 promoter---exon1---intron---exon2---SE---3'region---
   ---T7 promoter---exon1---intron---exon2---3'region---SE---3'region---
   ---T7 promoter---exon1---intron---exon2---3'region---SE---
4. Constructs with combinations of the constructs listed in 1–3.
5. Constructs with various structural elements:
   ---T7 promoter---exon1---SE1---intron---exon2---SE2---3'region
   ---T7 promoter---exon1---SE1---exon1---intron---SE2---intron---exon2---SE3---3'region---

The constructs in 1. here in particular serve to detect whether it was possible to remove exon1 from the intron sequence during the splicing process. The construct in 2. serves to detect directly a removed intron sequence. The constructs under 3. serve to detect whether it was possible to remove exon2 successfully from the intron sequence. A combination of the constructs according to 4. serves to detect the individual intermediates and end products during the splicing process. Exon1 is generally an exon located 5' of the intron and exon2 is generally an exon located 3' of the intron.

The constructs under 5. comprise various additional recognition sequences which may, on the one hand, relate to various detection systems and which may, on the other hand, facilitate binding of the nucleic acid to a solid phase via their binding partners. Thus it is possible, for example, to introduce a probe-binding nucleic acid into the 3' region for immobilizing and, at the same time, another probe-binding nucleic acid into exon1 (see 5., first construct) for detecting the splicing process. Moreover, it is possible to introduce, for example, three different nucleic acids which serves, firstly, to immobilize the entire nucleic acid and, secondly, to detect the removed intron and to detect the linkage of exon1 to the remaining nucleic acid (see 5., second construct). The location of the individual probe-binding nucleic acids listed, by way of example, under 5. may vary according to the above-described constructs under 1.–4. In addition, the exact location of the individual probe-binding nucleic acids is variable.

In another embodiment, therefore, the nucleic acid, preferably the spliceable nucleic acid, in particular a nucleic acid according to any of the above-described embodiments, is bound to a solid phase directly covalently or indirectly via a structural element and binding partner of the structural element or by means of hybridization.

The direct covalent binding may take place, for example, via the 3' terminal cis-diol group of the ribose backbone of the nucleic acid. It is possible, for example, to bind an RNA to hydrazine groups of the solid phase after periodate oxidation of the vicinal 2', 3' hydroxyl groups of the 3' terminal ribose. For indirect binding suitable linkers such as, for example, biotin linkers or dicarboxylic acid linkers are also suitable. As already stated above, however, the nucleic acid may also be bound via a binding partner, for example via theophylline, xanthine or an aminoglycoside such as tobramycin and/or via a nucleic acid binding protein such as, for example, IBP.

Suitable for immobilizing a nucleic acid to a support-bound ligand is, for example, in the case of theophylline as support-bound binding partner, the theophylline aptamer Th ($K_d$=0.9 $\mu$M) (see, for example, Jenison, R. G. et al. (1994) supra) or in the case of tobramycin as support-bound binding partner, the minimal version of the tobramycin aptamer To ($K_d$=0.2 $\mu$M) (Hamasaki, K. et al. (1998) supra). The sequences of the two aptamers are preferably:

Th: AAGUGAUACCAGCAUCGUCUUGAUGC-CCUUGGCAGCACUU (40mer, SEQ ID No.:1)
To: GGCUUAGUAUAGCGAGGUUUAGCUA-CACUCGUGCUGAGCC (40mer, SEQ ID No.:2)

The solid phase here is, for example, ceramic, metal, in particular noble metal, glass, plastic or polysaccharides, for example an agarose polymer.

However, probe-binding nucleic acids, for example aptamers, are also suitable for binding labeled probes, as a result of which it is possible, for example, to detect and also quantify the aptamer-containing nucleic acid. It is possible, for example, to react tobramycin with commercially available, NH$_2$-reactive fluorescent dyes (Wang, Y. et al. (1996) Biochemistry 35, 12338–12346). In the case of theophylline, preference is given to preparing a 1-aminoalkyl or 1-thioalkyl derivative of 3-methylxanthine, which can bind to the aptamer (Jenison, R. D. et al. (1994), supra).

According to the present invention, the spliceable nucleic acid is any nucleic acid which can be spliced, preferably an RNA, for example in the form of a "pre-mRNA" or in the form of a DNA comprising RNA sections. If the RNA is to comprise additional probe-binding sequences as already described in more detail above, it is advantageous if said probe-binding sequences are located on both exon sides at least approx. 25 nucleotides from the particular splicing site, on the intron side at least approx. 17 nucleotides from the branchpoint and/or at least approx. 7 nucleotides from the 5' splicing site. This generally ensures that the additional probe-binding sequences cannot disturb the splicing reactions.

An example of a spliceable nucleic acid, which is suitable for splicing in the human system, is the MINX model pre-mRNA (MINX=miniature wild type substrate;

Zillmann, M., Zapp, M. L., Berget, S. M. (1998), Mol. Cell. Biol., 8:814–21). It is preferably possible to introduce into the MINX-encoding DNA a further probe-binding nucleic acid suitable for detection or immobilization, as already described above, with the restriction enzyme cleavage site preferably being retained. This makes it possible to incorporate, if required, in a further cloning step another identical or different probe-binding nucleic acid for detection or for immobilization, in order to be able to enhance the fluorescence signals or to tighten binding to the solid phase.

Pre-mRNA is immobilized, for example, by inserting the Th or To aptamers at the 3' end of pre-mRNA exon2 and covalently binding the corresponding binding partner to the solid phase. The corresponding coding nucleic acid sequences are depicted in FIGS. 1A (SEQ ID NO:3) and 1B (SEQ ID NO:4).

In this context, for example, the appropriate aptamer sequence is inserted as DNA oligonucleotide into the BamHI cleavage site of the coding Minx DNA, i.e. between positions 219 and 220 of the corresponding Minx pre-mRNA.

As already mentioned above, it is also possible to insert probe-binding nucleic acids into the pre-mRNA intron structure, said nucleic acids being liberated by splicing and thus being absent in the, for example immobilized, mRNA. Constructs of this kind are therefore suitable for detecting an inhibition of splicing in the first step, i.e. opening of mRNA and lariat formation, or in the second step, i.e. removal of the lariat. In the case of an inhibition of the splicing process, the probe-binding nucleic acids would not be removed from the pre-mRNA and could therefore be detected, for example, after immobilization of the pre-mRNA. Examples of suitable nucleic acid constructs are depicted in the form of their coding sequences in FIG. 2A (SEQ ID NO:5) and FIG. 2B (SEQ ID NO:6).

To this end, for example, the appropriate aptamer sequence is inserted as DNA oligonucleotide into the PstI cleavage site of the coding Minx DNA, i.e. between positions 88 and 89 of the corresponding pre-mRNA.

As already described in more detail above, the spliceosome opens in the first splicing step the linkage between exon1 and intron at the 5' splicing site of the intron. Only in the second splicing step are exon1 and exon2 covalently linked. As a result, exon1 is no longer linked to the mRNA during the first step of the splicing reaction and is thus removable from the splicing reaction. In connection with constructs which have, for example, an aptamer structure in the intron, it is therefore possible to make a statement on whether, for example, an inhibition has occurred in the first splicing step. If, for example, two different aptamers which recognize different probes are incorporated at the 5' end of exon1 and into the intron of the pre-mRNA, then it is possible to follow both the first splicing step and the second splicing step in a test system. Examples of suitable nucleic acid constructs are depicted in the form of their coding sequences in FIG. 3A (SEQ ID NO:7) and FIG. 3B (SEQ ID NO:8).

To this end, for example, the appropriate aptamer sequence is inserted as DNA oligonucleotide into the EcoRI cleavage site of the coding Minx DNA, i.e. between positions 9 and 10 of the corresponding pre-mRNA.

For studies in the yeast system it is possible, for example, to start from the pre-mRNA for yeast U3 (Mougin, A. et al. (1996), RNA, 2: 1079–93) and to incorporate, for example, suitable aptamers such as, for example, the above-described theophylline or tobramycin aptamers. Examples of suitable nucleic acid constructs are depicted in the form of their coding sequences in FIGS. 4A to 4C (SEQ ID NOs:9, 10 and 11, respectively).

The nucleic acid construct according to FIG. 4A (SEQ ID NO:9) is prepared, for example, by inserting a suitable aptamer as DNA oligonucleotide into the SacII cleavage site of the coding U3 DNA, i.e. between positions 22 and 23 of the pre-U3 RNA.

The nucleic acid construct according to FIG. 4B (SEQ ID NO:10) is prepared, for example, by inserting a suitable aptamer as DNA oligonucleotide into the BstNI cleavage site of the coding U3 DNA, i.e. between positions 105 and 106 of the pre-U3 RNA.

The nucleic acid sequence according to FIG. 5A (SEQ ID NO:12) is an example of a nucleic acid sequence with an iron responsive element (IRE) which is suitable for studies in the human system. The IRE is inserted here at the 3' end of exon2 in analogy to the above-described aptamers.

For studies in the yeast system it is possible to insert an IRE element, for example, at the 3' end of exon2 of pre-U3RNA, as depicted in FIG. 5B (SEQ ID NO:13).

The present invention therefore further relates to a spliceable nucleic acid splicing, as illustrated by way of example above, and to the use thereof for preparing a test system.

The studies of the individual splicing reactions with the aid of a test system of the invention are commonly carried out by using a composition comprising the individual splicing components, preferably small nuclear ribonucleoprotein particle (snRNP) components and non-snRNP components. The snRNP components particularly comprise U1, U2, U4, U5 and/or U6 proteins. Preference is given in particular to using appropriate cell extracts, in particular eukaryotic cell extracts, for the studies. It is possible, for example, to obtain the cell extracts from animal cells, in particular mammalian cells, especially Hela cells, in particular from nuclear extracts of HeLa cells or cell extracts of fungi, in particular yeasts, according to methods generally known to the skilled worker (see examples). The cell extracts generally comprise all important factors in order to be able to carry out splicing in vitro.

It is essential for carrying out the studies to use further aids such as, for example, buffer solutions, stabilizers and/or energy equivalents, in particular ATP.

The present invention therefore also relates to a method for preparing a test system in which at least one immobilized spliceable nucleic acid and at least one gel-free detection system and also, where appropriate, at least one composition comprising splicing components and, where appropriate, further aids are combined. Preferred embodiments of the individual components have already been described in more detail above.

The present invention further relates to a method for finding an active substance, which comprises
  (a) incubating one or more identical or different immobilized nucleic acid(s) with at least one spliceable nucleic acid sequence in the presence of at least one substance to be studied and at least one composition comprising splicing components and, where appropriate, further aids under suitable conditions, and
  (b) detecting the splicing product which may have formed by means of a gel-free detection system.

Preferred individual components of the method of the invention have already been described in more detail above.

The active substance here may be a pharmaceutically active compound, a fungicide, a herbicide, a pesticide and/or an insecticide, and is preferably an antibiotic. The substance to be studied is generally a naturally occurring, a naturally occurring and chemically modified, and/or a synthetic substance. The method of the invention makes it possible in particular to screen "combinatorial substance libraries" in a simple and rapid manner.

In the introduction of the description it was already indicated that various disorders can be attributed to a disruption of the splicing mechanism. The present invention is therefore also suitable for diagnosing a disorder.

The present invention therefore further relates to a method for diagnosing a disorder, which comprises
(a) incubating one or more identical or different immobilized nucleic acid(s) with at least one spliceable nucleic acid in the presence of at least one composition comprising splicing components and, where appropriate, further aids under suitable conditions, and
(b) detecting the splicing product which may have formed by means of a gel-free detection system.

The disorders to be diagnosed here are preferably genetic disorders, cancers and/or viral diseases, in particular Graves' disease, spinal muscular atrophy, β' thalassemia, cancers related to the c-erb oncogene, hepatitis C infections and/or Herpes simplex virus infections. The composition comprising splicing components may in this case be a treated or untreated tissue sample of a patient, for example.

The following figures and examples are intended to describe the invention in more detail without restricting it. The constructs in DNA sequences are shown. The RNAs capable of being spliced can be generated by in vitro transcription which is described further below.

DESCRIPTION OF FIGURES

FIG. 1A shows the coding nucleic acid sequence into which a Th aptamer was inserted at the 3' end of exon2 of a pre-mRNA coding for Minx (SEQ ID NO:3).

FIG. 1B shows the coding nucleic acid sequence into which a To aptamer was inserted at the 3' end of exon2 of a pre-mRNA coding for Minx (SEQ ID NO:4).

FIG. 2A shows the coding nucleic acid sequence into which a Th aptamer was inserted into the intron of a pre-mRNA coding for Minx (SEQ ID NO:5).

FIG. 2B shows the coding nucleic acid sequence into which a To aptamer was inserted into the intron of a pre-mRNA coding for Minx (SEQ ID NO:6).

FIG. 3A shows the coding nucleic acid sequence into which a Th aptamer was inserted at the 5' end of exon1 of a pre-mRNA coding for Minx (SEQ ID NO:7).

FIG. 3B shows the sequence of an RNA into which a Th aptamer was inserted at the 5' end of exon1 of a pre-mRNA coding for Minx (SEQ ID NO:8).

FIG. 4A shows the coding nucleic acid sequence coding for a U3 pre-mRNA. At the 5' end of exon1 an insertion site for a Th or To aptamer is indicated (SEQ ID NO:9).

FIG. 4B shows the coding nucleic acid sequence coding for a U3 pre-mRNA. In the intron an insertion site for a Th or To aptamer is indicated (SEQ ID NO:10).

FIG. 4C shows the coding nucleic acid sequence coding for a U3 pre-mRNA. At the 3' end of exon2 an insertion site for a Th or To aptamer is indicated (SEQ ID NO:11).

FIG. 5A shows the coding nucleic acid sequence coding for a Minx pre-mRNA. At the 3' end of exon2 a the sequence for IRE has been inserted (SEQ ID NO:12).

FIG. 5B shows the coding nucleic acid sequence coding for a U3 pre-mRNA. At the 3' end of exon2 a the sequence for IRE has been inserted (SEQ ID NO:13).

FIG. 6 shows the time course of the splicing of MINX and MINX-IRE pre-mRNA by HeLa nuclear extract.

In vitro-transcribed MINX (lanes 1–5) and MINX-IRE (lanes 6–10) pre-mRNAs were incubated with HeLa nuclear extract for the period indicated in the figure. The samples were then fractionated by means of polyacrylamide/urea gel electrophoresis and 32P-labeled RNA was detected with the aid of autoradiography. Multiple bands in the case of IRE-containing RNA (lanes 6–10) can be explained by incomplete IRE denaturation.

EXAMPLES

1. The RNA Construct

The mRNA to be spliced comprises at least two exons which are separated by an intron. In addition to these sequences, sequences which are suitable for facilitating specific recognition by RNA binding proteins or low molecular weight compounds are included. Via coupling of said binding proteins or compounds to a matrix, the mRNA is selectively bound to the matrix. Alternatively, the mRNA may also be coupled covalently via 3' OH groups of the ribose directly to the matrix.

2. Preparation of Nuclear Extracts 2.1 Nuclear Extracts From Mammalian Cells Nuclear extracts are prepared from mammalian cells by using cell cultures of Hela cells. To this end, the cells are sedimented from the culture medium by centrifugation (1000×g, 10 min) and washed with phosphate buffer. The cell sediment is then taken up in five volumes of buffer A (10 mM HEPES, 1.5 mM $MgCl_2$, 10 mM KCl, 0.5 mM DTT, pH 7.9, 4° C.) and incubated for 10 minutes. The cells are again sedimented and taken up in two volumes of buffer A. This suspension is disrupted using a Dounce homogenizer (pestle B) (moving the pestle up and down 10 times). The nuclei are sedimented by centrifugation. Finally, the nuclei are again taken up in buffer A and centrifuged at 25000×g for 20 minutes. The sediment is taken up in 3 ml of buffer B (20 mM HEPES, 25% (v/v) glycerol, 0.42 M NaCl, 1.5 mM $MgCl_2$, 0.2 mM EDTA, 0.5 mM phenylmethylsulfonyl fluoride (PMSF), 0.5 mM DTT, pH 7.9) and disrupted again using the Dounce homogenizer. The suspension forming is incubated on a magnetic stirrer for 30 minutes and then centrifuged at 25000×g for 30 minutes. This is again followed by centrifugation at 25000×g (30 min). The clear supernatant is dialyzed against 50 volumes of buffer C (20 mM HEPES, 20% (v/v) glycerol, 0.1 M KCl, 0.2 mM EDTA, 0.5 mM PMSF, 0.5 mM DTT, pH 7.9). The dialyzate is centrifuged (25000×g, 20 min) and the resulting supernatant can be stored as nuclear extract in liquid nitrogen (Dignam; J. D. et al. (1983) Nucleic Acid Res., 11, 1475).

2.2 Cell Extracts From Yeast Cells

Cell extracts from yeast cells are prepared in a very similar way. Yeast cells of a protease-deficient strain (BJ926, EJ101 or similar strains) are sedimented by centrifugation (1 500×g, 5 min, 4° C.) in the logarithmic growth phase. The cells are resuspended in two to four volumes of ice cold water and again centrifuged at 1 500×g (5 min, 4° C.). The cells are then taken up in one volume of zymolyase buffer (50 mM Tris HCL, 10 mM $MgCl_2$, 1M sorbitol, 30 mM DTT, pH 7.5) and incubated at room temperature for 30 minutes. The cells are removed by centrifugation (1 500×g, 5 min, 4° C.), taken up in three volumes of zymolyase buffer with 2 mg (200 U) of zymolyase 100 T and incubated on a shaker (50 rpm) at 30° C. for 40 minutes. The spheroblasts formed are removed by centrifugation (1 500×g, 5 min, 4° C.) and washed once in 2 ml of ice cold zymolyase buffer. The sediment is washed with two volumes of lysis buffer (50 mM Tris HCl, 10 mM $MgSO_4$, 1 mM EDTA, 10 mM potassium acetate, 1 mM DTT, protease inhibitors, 1 mM PMSF, pH 7.5) and finally taken up in one volume of lysis buffer. The spheroblasts are then lysed in a Dounce homogenizer by moving the pestle up and down 15 to 20 times (distance 1–2 μm). The same volume of extraction buffer (lysis buffer+0.8 M ammonium sulfate, 20% (v/v) glycerol) is added to the lysate and the mixture is incubated on an end-over-end shaker for 15–30 minutes (4° C.). This is followed by centrifugation at 100 000×g for 90 minutes (4° C.). The supernatent is dialyzed against one hundred volumes of storage buffer (20 mM Tris HCl, 0.1 mM EDTA, 10% (v/v) glycerol, 100 mM KCl, 1 mM DTT, protease inhibitors, 1 mM PMSF, pH 7.5). The dialyzate is removed by centrifugation at 10 000×g (4° C.) and the supernatant is stored in liquid nitrogen (Dunn, B. & Wobbe, C. R. (1994) Preparation of protein extracts from yeast, In: Ausubel, F. M. et al. (eds.) Current Protocols in Molecular Biolody, 2nd Volume, John Wiley and Sons, Inc., USA, pp. 13.13.1–13.13.9).

3. In Vitro Splicing of Constructs with IRE in a Test System

Excising the intron from the RNA sequence leads at the boundary of the two now linked exons to a nucleotide sequence which is not present in the unspliced pre-mRNA (neosequence). This sequence is utilized for generating complementary nucleotide sequences which selectively bind only to said neosequence. Covalent binding of fluorescent dyes, biotin, igoxigenin or similar molecules or radiolabeling indirectly detects the plicing carried out. The assay is analyzed in a suitable analyzer (ELISA reader, fluorimeter, etc.).

All experiments described were carried out according to standard methods, as are described in (Eperon, I. C. and Krainer, A. R. (1994) Splicing of mRNA precursors in mammalian cells. In RNA Processing, vol. I—A Practical Approach (B. D. Hames and S. J. Higgins, eds.) Oxford: IRL Press, pp. 57–101).

3.1 In Vitro Transcription Procedure

The construct described in FIG. 5A (SEQ ID NO:12) was transcribed from the plasmid coding therefor into the corresponding mRNA by means of in vitro transcription. Likewise, the corresponding construct without IRE sequence was used in the experiments as a control and for subsequent comparison.

Prior to that, the constructs were cloned into vector pGEM-3Zf (Pharmacia) and propagated in *E. coli*. The plasmids were purified and adjusted to the desired concentration with the aid of standard technologies. Prior to the use in the in vitro transcription, the plasmids were linearized with the aid of restriction enzymes.

The reaction was carried out under the following conditions:

5 μl of 5×transcription buffer (200 mM Tris-HCl pH 7.9, 30 mM $MgCl_2$,
10 mM spermidine, 50 mM NaCl)
1 μl of BSA (1 mg/ml)
1 μl of RNAsin
2.5 μl of DTT (100 mM)
1 μl of NTPs (ATP, GTP, CTP at 2.5 mM and UTP at 1.25 mM)
2 μl of $^{32}$P-UTP (3000 Ci/mM)
2 μl of MINX plasmid linearized (1 mg/ml)
2.5 μl of GpppG-Cap (1 mM)
2 μl of SP6 polymerase
ad 25 μl with $H_2O$ The transcription mixture was incubated at 37° C. for 2 h and then purified via a preparative gel according to standard methods. The labeled RNA was found by applying an X-ray film for 1 minute and the band was cut out by means of a scalpel. The gel fragment was cut and the RNA was extracted from the gel at 4° C. overnight using elution buffer (500 mM Na acetate pH 5, 1 mM EDTA pH 8, 2.5% phenol/chloroform).

3.2 Splicing Reaction Procedure

7 μl of HeLa cell nuclear extract (=35% v/v) were incubated with 3.25 mM $MgCl_2$, 35 mM KCl, 2 mM ATP, 20 mM phosphocreatine, 1 U/μl RNAsin and 30 000–50 000 cpm of MINX pre-mRNA (Zillmann et al., 1988, Molecular and Cellular Biology, 8: 814) in a reaction volume of 20 μl at 30° C. for 0, 10, 20, 30 and 40 minutes. Pre-mRNA which did not contain IRE was used for comparison. The reactions were then stopped by adding 400 l of proteinase K buffer (100 mM Tris-HCl, pH 7.5, 12.5 mM EDTA, 150 mM NaCl, 1% SDS, 0.1 mg proteinase K). The samples were extracted with 400 μl of phenol/chloroform and the aqueous phase was precipitated with 2.5 volumes of ethanol and 1/10 volume of 3M sodium acetate (pH 5.2) at −20° C. The RNA was removed by centrifugation and washed with 70–80% ethanol. After another centrifugation, the RNA was dried.

The dried RNA was taken up in 5 μl of sample buffer (0.5×TBE, 80% (v/v) formamide, 0.1% (w/v) xylene cyanol and 0.1% (w/v) bromophenol blue), heated at 65° C. for 10 minutes, cooled on ice and then fractionated by means of an 8% strength polyacrylamide gel. The fractionated RNA was detected by means of autoradiography (see FIG. 6).

Lanes 1–5 of FIG. 6 show the time course (0, 10, 20, 30, 40 minutes) of the splicing reaction of MINX pre-mRNA without IRE at the 3' OH end. The figure shows that after approx. 20 minutes a large part of pre-mRNA has been transformed into mature mRNA. Lanes 6–10 show the same experiment with pre-mRNA modified by IRE at the 3' OH end. Here too, a distinct splicing reaction can be seen after an incubation time of 20 minutes.

SEQUENCE LISTING

<160> NUMBER OF SEQ ID NOS: 27

<210> SEQ ID NO 1
<211> LENGTH: 40
<212> TYPE: RNA
<213> ORGANISM: Artificial Sequence
<220> FEATURE:
<223> OTHER INFORMATION: Aptamer

```
<400> SEQUENCE: 1
aagugauacc agcaucgucu ugaugcccuu ggcagcacuu                            40

<210> SEQ ID NO 2
<211> LENGTH: 40
<212> TYPE: RNA
<213> ORGANISM: Artificial Sequence
<220> FEATURE:
<223> OTHER INFORMATION: Aptamer

<400> SEQUENCE: 2
ggcuuaguau agcgagguuu agcuacacuc gugcugagcc                            40

<210> SEQ ID NO 3
<211> LENGTH: 283
<212> TYPE: DNA
<213> ORGANISM: Artificial Sequence
<220> FEATURE:
<223> OTHER INFORMATION: pre-mRNA

<400> SEQUENCE: 3
taatacgact cactataggg cgaattcgag ctcgcccact cttggatcgg aaacccgtcg      60
gcctccgaac ggtaagagcc tagcatgtag aactggttac ctgcagccca agcttgctgc    120
acgtctaggg cgcagtagtc cagggtttcc ttgatgatgt catacttatc ctgtcccttt    180
tttttccaca gctcgcggtt gaggacaaac tcttcgcggt cttticcagtg gggatccaag   240 tgataccagc atcgtcttga tgcccttggc agcacttgga tcc                      283

<210> SEQ ID NO 4
<211> LENGTH: 283
<212> TYPE: DNA
<213> ORGANISM: Artificial Sequence
<220> FEATURE:
<223> OTHER INFORMATION: pre-mRNA

<400> SEQUENCE: 4
ttaatacgac tcactatagg gcgaattcga gctcgcccac tcttggatcg gaaacccgtc     60
ggcctccgaa cggtaagagc ctagcatgta gaactggtta cctgcagccc aagcttgctg   120
cacgtctagg gcgcagtagt ccagggtttc cttgatgatg tcatacttat cctgtccctt   180 tttttttccac agctcgcggt tgaggacaaa ctcttcgcgg tctttccagt ggggatcggc   240
ttagtatagc gaggtttagc tacactcgtg ctgagccgga tcc                      283

<210> SEQ ID NO 5
<211> LENGTH: 282
<212> TYPE: DNA
<213> ORGANISM: Artificial Sequence
<220> FEATURE:
<223> OTHER INFORMATION: pre-mRNA

<400> SEQUENCE: 5
taatacgact cactataggg cgaattcgag ctcgcccact cttggatcgg aaacccgtcg     60
gcctccgaac ggtaagagcc tagcatgtag aactggttac ctgcaaagtg ataccagcat   120
cgtcttgatg cccttggcag cacttctgca gcccaagctt gctgcacgtc tagggcgcag   180
tagtccaggg tttccttgat gatgtcatac ttatcctgtc ccttttttt ccacagctcg    240 cggttgagga caaactcttc gcggtctttc cagtggggat cc                      282

<210> SEQ ID NO 6
<211> LENGTH: 282
```

```
<212> TYPE: DNA
<213> ORGANISM: Artificial Sequence
<220> FEATURE:
<223> OTHER INFORMATION: pre-mRNA

<400> SEQUENCE: 6
taatacgact cactataggg cgaattcgag ctcgcccact cttggatcgg aaacccgtcg      60
gcctccgaac ggtaagagcc tagcatgtag aactggttac ctgcaggctt agtatagcga     120
ggtttagcta cactcgtgct gagccctgca gcccaagctt gctgcacgtc tagggcgcag     180
tagtccaggg tttccttgat gatgtcatac ttatcctgtc ccttttttt ccacagctcg      240
cggttgagga caaactcttc gcggtctttc cagtggggat cc                       282

<210> SEQ ID NO 7
<211> LENGTH: 282
<212> TYPE: DNA
<213> ORGANISM: Artificial Sequence
<220> FEATURE:
<223> OTHER INFORMATION: pre-mRNA

<400> SEQUENCE: 7
taatacgact cactataggg cgaattaagt gataccagca tcgtcttgat gcccttggca      60
gcacttgaat tcgagctcgc ccactcttgg atcggaaacc cgtcggcctc cgaacggtaa     120
gagcctagca tgtagaactg gttacctgca gcccaagctt gctgcacgtc tagggcgcag     180
tagtccaggg tttccttgat gatgtcatac ttatcctgtc ccttttttt ccacagctcg      240
cggttgagga caaactcttc gcggtctttc cagtggggat cc                       282

<210> SEQ ID NO 8
<211> LENGTH: 282
<212> TYPE: DNA
<213> ORGANISM: Artificial Sequence
<220> FEATURE:
<223> OTHER INFORMATION: pre-mRNA

<400> SEQUENCE: 8
taatacgact cactataggg cgaattggct tagtatagcg aggtttagct acactcgtgc      60
tgagccgaat tcgagctcgc ccactcttgg atcggaaacc cgtcggcctc cgaacggtaa     120
gagcctagca tgtagaactg gttacctgca gcccaagctt gctgcacgtc tagggcgcag     180
tagtccaggg tttccttgat gatgtcatac ttatcctgtc ccttttttt ccacagctcg      240
cggttgagga caaactcttc gcggtctttc cagtggggat cc                       282

<210> SEQ ID NO 9
<211> LENGTH: 563
<212> TYPE: DNA
<213> ORGANISM: Artificial Sequence
<220> FEATURE:
<223> OTHER INFORMATION: pre-mRNA

<400> SEQUENCE: 9
taatacgact cactataggg cgaattggag ctccaccgcc cgcggtggcg gccgctctag      60
aactagtgga tccgtcgact gacttcagta tgtaatatac cccaaacatt ttacccacaa     120
aaaaccagga tttgaaacta tagcatctaa aagtcttagg tactagagtt ttcatttcgg     180
agcaggcttt tgaaaaatt taattcaacc attgcagcag cttttgacta acacattcta     240
cagtaggatc atttctatag gaatcgtcac tctttgactc ttcaaaagag ccactgaatc     300
caacttggtt gatgagtccc ataaccttg taccccagag tgagaaaccg aaattgaatc     360
```

| | |
|---|---:|
| taaattagct tggtccgcaa tccttagcgt tcggccatct ataattttga ataaaatttt | 420 |
| tgctttgccg ttgcatttgt agttttttcc tttggaagta attacaatat tttatggcgc | 480 |
| gatgattctt gacccatcct atgtacttct tttttgaagg atagggctc tatgggtggg | 540 |
| tacaaatggc agtctgacaa gtt | 563 |

<210> SEQ ID NO 10
<211> LENGTH: 562
<212> TYPE: DNA
<213> ORGANISM: Artificial Sequence
<220> FEATURE:
<223> OTHER INFORMATION: pre-mRNA

<400> SEQUENCE: 10

| | |
|---|---:|
| taatacgact cactataggg cgaattggag ctccaccgcg gtggcggccg ctctagaact | 60 |
| agtggatccg tcgactgact tcagtatgta atataccccca acatttttac ccacaaaaaa | 120 |
| ccaccaggat ttgaaactat agcatctaaa agtcttaggt actagagttt tcatttcgga | 180 |
| gcaggctttt tgaaaaattt aattcaacca ttgcagcagc ttttgactaa cacattctac | 240 |
| agtaggatca tttctatagg aatcgtcact ctttgactct tcaaagagc cactgaatcc | 300 |
| aacttggttg atgagtccca taacctttgt accccagagt gagaaaccga aattgaatct | 360 |
| aaattagctt ggtccgcaat ccttagcgtt cggccatcta aattttgaa taaaattttt | 420 |
| gctttgccgt tgcatttgta gttttttcct ttggaagtaa ttacaatatt ttatggcgcg | 480 |
| atgattcttg acccatccta tgtacttctt ttttgaaggg atagggctct atgggtgggt | 540 |
| acaaatggca gtctgacaag tt | 562 |

<210> SEQ ID NO 11
<211> LENGTH: 559
<212> TYPE: DNA
<213> ORGANISM: Artificial Sequence
<220> FEATURE:
<223> OTHER INFORMATION: pre-mRNA

<400> SEQUENCE: 11

| | |
|---|---:|
| taatacgact cactataggg cgaattggag ctccaccgcg gtggcggccg ctctagaact | 60 |
| agtggatccg tcgactgact tcagtatgta atataccccca acatttttac ccacaaaaaa | 120 |
| ccaggatttg aaactatagc atctaaaagt cttaggtact agagttttca tttcggagca | 180 |
| ggcttttga aaaatttaat tcaaccattg cagcagcttt tgactaacac attctacagt | 240 |
| aggatcattt ctataggaat cgtcactctt tgactcttca aaagagccac tgaatccaac | 300 |
| ttggttgatg agtcccataa cctttgtacc ccagagtgag aaaccgaaat tgaatctaaa | 360 |
| ttagcttggt ccgcaatcct tagcgttcgg ccatctataa ttttgaataa aattttgct | 420 |
| ttgccgttgc atttgtagtt ttttcctttg gaagtaatta catatttta tggcgcgatg | 480 |
| attcttgacc catcctatgt acttctttt tgaagggata gggctctatg ggtgggtaca | 540 |
| aatggcagtc tgacaagtt | 559 |

<210> SEQ ID NO 12
<211> LENGTH: 277
<212> TYPE: DNA
<213> ORGANISM: Artificial Sequence
<220> FEATURE:
<223> OTHER INFORMATION: pre-mRNA

<400> SEQUENCE: 12

| | |
|---|---:|
| taatacgact cactataggg cgaattcgag ctcgcccact cttggatcgg aaacccgtcg | 60 |

```
gcctccgaac ggtaagagcc tagcatgtag aactggttac ctgcagccca agcttgctgc    120
acgtctaggg cgcagtagtc cagggttttcc ttgatgatgt catacttatc ctgtcccttt    180 ttttccaca gctcgcggtt gaggacaaac tcttcgcggt ctttccagtg gggatcgggg    240
atcctgcttc aacagtgctt ggacggatcc tctagac                              277
```

<210> SEQ ID NO 13
<211> LENGTH: 600
<212> TYPE: DNA
<213> ORGANISM: Artificial Sequence
<220> FEATURE:
<223> OTHER INFORMATION: pre-mRNA

<400> SEQUENCE: 13

```
taatacgact cactataggg cgaattggag ctccaccgcg gtggcggccg ctctagaact     60
agtggatccg tcgactgact tcagtatgta atataccca acatttac ccacaaaaa       120 ccaggatttg aaactatagc atctaaaagt cttaggtact agagttttca tttcggagca    180 ggcttttga aaatttaat tcaaccattg cagcagcttt tgactaacac attctacagt      240
aggatcattt ctataggaat cgtcactctt tgactcttca aaagagccac tgaatccaac    300
ttggttgatg agtcccataa cctttgtacc ccagagtgag aaaccgaaat tgaatctaaa    360
ttagcttggt ccgcaatcct tagcgttcgg ccatctataa ttttgaataa aattttgct     420 ttgccgttgc atttgtagtt ttttcctttg gaagtaatta caatatttta tggcgcgatg    480
attcttgacc catcctatgt acttcttttt tgaagggata gggctctatg ggtgggtaca    540
aatggcagtc tgacaagttg gggatcctgc ttcaacagtg cttggacgga tcctctagac    600
```

<210> SEQ ID NO 14
<211> LENGTH: 244
<212> TYPE: DNA
<213> ORGANISM: Artificial Sequence
<220> FEATURE:
<223> OTHER INFORMATION: pre-mRNA

<400> SEQUENCE: 14

```
tcttggatcg gaaacccgtc ggcctccgaa cggtaagagc ctagcatgta gaactggtta     60
cctgcagccc aagcttgctg cacgtctagg gcgcagtagt ccagggtttc cttgatgatg    120
tcatacttat cctgtccctt ttttttccac agctcgcggt tgaggacaaa ctcttcgcgg    180
tctttccagt ggggatccaa gtgataccag catcgtcttg atgcccttgg cagcacttgg    240
atcc                                                                  244
```

<210> SEQ ID NO 15
<211> LENGTH: 246
<212> TYPE: DNA
<213> ORGANISM: Artificial Sequence
<220> FEATURE:
<223> OTHER INFORMATION: pre-mRNA

<400> SEQUENCE: 15

```
cactcttgga tcggaaaccc gtcggcctcc gaacggtaag agcctagcat gtagaactgg     60
ttacctgcag cccaagcttg ctgcacgtct agggcgcagt agtccagggt ttccttgatg    120
atgtcatact tatcctgtcc cttttttttc cacagctcgc ggttgaggac aaactcttcg    180
cggtctttcc agtgggggatc ggcttagtat agcgaggttt agctacactc gtgctgagcc    240
ggatcc                                                                246
```

<210> SEQ ID NO 16
<211> LENGTH: 246
<212> TYPE: DNA
<213> ORGANISM: Artificial Sequence
<220> FEATURE:
<223> OTHER INFORMATION: pre-mRNA

<400> SEQUENCE: 16

```
cactcttgga tcggaaaccc gtcggcctcc gaacggtaag agcctagcat gtagaactgg      60
ttacctgcaa agtgatacca gcatcgtctt gatgcccttg gcagcacttc tgcagcccaa     120
gcttgctgca cgtctagggc gcagtagtcc agggtttcct tgatgatgtc atacttatcc     180
tgtccctttt ttttccacag ctcgcggttg aggacaaact cttcgcggtc tttccagtgg     240
ggatcc                                                                246
```

<210> SEQ ID NO 17
<211> LENGTH: 247
<212> TYPE: DNA
<213> ORGANISM: Artificial Sequence
<220> FEATURE:
<223> OTHER INFORMATION: pre-mRNA

<400> SEQUENCE: 17

```
ccactcttgg atcggaaacc cgtcggcctc cgaacggtaa gagcctagca tgtagaactg      60
gttacctgca ggcttagtat agcgaggttt agctacactc gtgctgagcc ctgcagccca     120
agcttgctgc acgtctaggg cgcagtagtc cagggtttcc ttgatgatgt catacttatc     180
ctgtcccttt ttttccaca gctcgcggtt gaggacaaac tcttcgcggt ctttccagtg      240
gggatcc                                                               247
```

<210> SEQ ID NO 18
<211> LENGTH: 256
<212> TYPE: DNA
<213> ORGANISM: Artificial Sequence
<220> FEATURE:
<223> OTHER INFORMATION: pre-mRNA

<400> SEQUENCE: 18

```
aagtgatacc agcatcgtct tgatgccctt ggcagcactt gaattcgagc tcgcccactc      60
ttggatcgga aacccgtcgg cctccgaacg gtaagagcct agcatgtaga actggttacc     120
tgcagcccaa gcttgctgca cgtctagggc gcagtagtcc agggtttcct tgatgatgtc     180
atacttatcc tgtccctttt ttttccacag ctcgcggttg aggacaaact cttcgcggtc     240
tttccagtgg ggatcc                                                     256
```

<210> SEQ ID NO 19
<211> LENGTH: 256
<212> TYPE: DNA
<213> ORGANISM: Artificial Sequence
<220> FEATURE:
<223> OTHER INFORMATION: pre-mRNA

<400> SEQUENCE: 19

```
ggcttagtat agcgaggttt agctacactc gtgctgagcc gaattcgagc tcgcccactc      60
ttggatcgga aacccgtcgg cctccgaacg gtaagagcct agcatgtaga actggttacc     120
tgcagcccaa gcttgctgca cgtctagggc gcagtagtcc agggtttcct tgatgatgtc     180
atacttatcc tgtccctttt ttttccacag ctcgcggttg aggacaaact cttcgcggtc     240
tttccagtgg ggatcc                                                     256
```

<210> SEQ ID NO 20
<211> LENGTH: 524
<212> TYPE: DNA
<213> ORGANISM: Artificial Sequence
<220> FEATURE:
<223> OTHER INFORMATION: pre-mRNA

<400> SEQUENCE: 20

```
ccgcggtggc ggccgctcta gaactagtgg atccgtcgac tgacttcagt atgtaatata      60
ccccaaacat tttacccaca aaaaccagg  atttgaaact atagcatcta aaagtcttag     120
gtactagagt tttcatttcg gagcaggctt tttgaaaaat ttaattcaac cattgcagca     180
gcttttgact aacacattct acagtaggat catttctata ggaatcgtca ctctttgact     240
cttcaaaaga gccactgaat ccaacttggt tgatgagtcc cataaccttt gtaccccaga     300
gtgagaaacc gaaattgaat ctaaattagc ttggtccgca atccttagcg ttcggccatc     360
tataattttg aataaaaatt ttgctttgcc gttgcatttg tagttttttc ctttggaagt     420
aattacaata ttttatggcg cgatgattct tgacccatcc tatgtacttc ttttttgaag     480
ggatagggct ctatgggtgg gtacaaatgg cagtctgaca agtt                      524
```

<210> SEQ ID NO 21
<211> LENGTH: 57
<212> TYPE: DNA
<213> ORGANISM: Artificial Sequence
<220> FEATURE:
<223> OTHER INFORMATION: pre-mRNA

<400> SEQUENCE: 21

```
tccgtcgact gacttcagta tgtaatatac cccaaacatt ttacccacaa aaacca          57
```

<210> SEQ ID NO 22
<211> LENGTH: 439
<212> TYPE: DNA
<213> ORGANISM: Artificial Sequence
<220> FEATURE:
<223> OTHER INFORMATION: pre-mRNA

<400> SEQUENCE: 22

```
ccaggatttg aaactatagc atctaaaagt cttaggtact agagttttca tttcggagca      60
ggcttttga  aaaatttaat tcaaccattg cagcagcttt tgactaacac attctacagt     120
aggatcattt ctataggaat cgtcactctt tgactcttca aaagagccac tgaatccaac     180
ttggttgatg agtcccataa cctttgtacc ccagagtgag aaaccgaaat tgaatctaaa     240
ttagcttggt ccgcaatcct tagcgttcgg ccatctataa ttttgaataa aaattttgct     300
ttgccgttgc atttgtagtt ttttcctttg gaagtaatta caatatttta tggcgcgatg     360
attcttgacc catcctatgt acttcttttt tgaagggata gggctctatg ggtgggtaca     420
aatggcagtc tgacaagtt                                                  439
```

<210> SEQ ID NO 23
<211> LENGTH: 490
<212> TYPE: DNA
<213> ORGANISM: Artificial Sequence
<220> FEATURE:
<223> OTHER INFORMATION: pre-mRNA

<400> SEQUENCE: 23

```
gtcgactgac ttcagtatgt aatataccccc aaacatttta cccacaaaaa accaggatttt     60
```

```
gaaactatag catctaaaag tcttaggtac tagagttttc atttcggagc aggcttttg      120 aaaaatttaa ttcaaccatt gcagcagctt ttgactaaca cattctacag taggatcatt    180
tctataggaa tcgtcactct ttgactcttc aaaagagcca ctgaatccaa cttggttgat    240
gagtcccata acctttgtac cccagagtga aaaccgaaa ttgaatctaa attagcttgg     300
tccgcaatcc ttagcgttcg gccatctata attttgaata aaaattttgc tttgccgttg    360
catttgtagt ttttccttt ggaagtaatt acaatatttt atggcgcgat gattcttgac     420
ccatcctatg tacttctttt ttgaagggat agggctctat gggtgggtac aaatggcagt    480
ctgacaagtt                                                           490
```

```
<210> SEQ ID NO 24
<211> LENGTH: 241
<212> TYPE: DNA
<213> ORGANISM: Artificial Sequence
<220> FEATURE:
<223> OTHER INFORMATION: pre-mRNA

<400> SEQUENCE: 24
cactcttgga tcggaaaccc gtcggcctcc gaacggtaag agcctagcat gtagaactgg    60
ttacctgcag cccaagcttg ctgcacgtct agggcgcagt agtccagggt ttccttgatg    120
atgtcatact tatcctgtcc cttttttttc cacagctcgc ggttgaggac aaactcttcg    180
cggtctttcc agtggggatc ggggatcctg cttcaacagt gcttggacgg atcctctaga    240
c                                                                    241
```

```
<210> SEQ ID NO 25
<211> LENGTH: 534
<212> TYPE: DNA
<213> ORGANISM: Artificial Sequence
<220> FEATURE:
<223> OTHER INFORMATION: pre-mRNA

<400> SEQUENCE: 25
tccgtcgact gacttcagta tgtaatatac cccaaacatt ttaccacaa aaaaccagga     60 tttgaaacta tagcatctaa aagtcttagg tactagagtt ttcatttcgg agcaggcttt    120
ttgaaaaatt taattcaacc attgcagcag cttttgacta acacattcta cagtaggatc    180
atttctatag gaatcgtcac tctttgactc ttcaaaagag ccactgaatc caacttggtt    240
gatgagtccc ataacctttg taccccagag tgagaaaccg aaattgaatc taaattagct    300
tggtccgcaa tccttagcgt tcggccatct ataattttga ataaaaattt tgctttgccg    360
ttgcatttgt agtttttttcc tttggaagta attacaatat tttatggcgc gatgattctt    420
gacccatcct atgtacttct ttttgaagg gatagggctc tatgggtggg tacaaatggc     480
agtctgacaa gttggggatc ctgcttcaac agtgcttgga cggatcctct agac          534
```

```
<210> SEQ ID NO 26
<211> LENGTH: 45
<212> TYPE: DNA
<213> ORGANISM: Artificial Sequence
<220> FEATURE:
<223> OTHER INFORMATION: Aptamer

<400> SEQUENCE: 26
aagtgatacc agcatcgtct tgatgccctt ggcagcactt gaatt                    45
```

```
<210> SEQ ID NO 27
<211> LENGTH: 45
```

```
<212> TYPE: DNA
<213> ORGANISM: Artificial Sequence
<220> FEATURE:
<223> OTHER INFORMATION: Aptamer

<400> SEQUENCE: 27
ggcttagtat agcgaggttt agctacactc gtgctgagcc gaatt              45
```

What is claimed is:

1. A test system for detecting a splicing reaction comprising
   (a) one or more identical or different nucleic acid(s), encompassing at least one spliceable nucleic acid, wherein the nucleic acid(s) is (are) immobilized on a solid phase,
   (b) at least one composition comprising splicing components,
   (c) at least one suitable detection probe,
   (d) at least one device for detecting binding of the detection probe, wherein the device does not comprise a gel.

2. The test system as claimed in claim 1 wherein the spliceable nucleic acid according to feature (a) comprises at least two exons which are separated by at least one intron.

3. The test system as claimed in claim 1 wherein the suitable detection probe according to feature (c) is a nucleic acid complementary to the spliceable nucleic acid, a low molecular weight compound which binds the spliceable nucleic acid or a peptide or protein which binds the spliceable nucleic acid.

4. The test system as claimed in claim 3 wherein the low molecular weight compound is selected from the group consisting of theophylline, xanthine and an aminoglycoside, and the nucleic acid-binding peptide or protein is an iron responsive element binding protein IBP.

5. The test system as claimed in claim 4 wherein the aminoglycoside is tobramycin.

6. The test system as claimed in claim 3 wherein the complementary nucleic acid is complementary to at least one intron, to at least one exon or to at least one exon/intron transition site.

7. The test system as claimed in claim 3 wherein the spliceable nucleic acid or the complementary nucleic acid comprises a recognition sequence for a nucleic acid-binding low molecular weight compound or for a nucleic acid-binding peptide or protein.

8. The test system as claimed in claim 7 wherein the recognition sequence for a nucleic acid-binding low molecular weight compound is an aptamer sequence.

9. The test system as claimed in claim 1 wherein the detection of the splicing reaction occurs by means of a label.

10. The test system as claimed in claim 9 wherein the label is a radio-label, a fluorescent dye, biotin, digoxigenin or an antibody.

11. The test system as claimed in claim 1 wherein the detection probe binds not directly to the spliceable nucleic acid, but to a probe-binding nucleic acid that is linked to the spliceable nucleic acid.

12. The test system as claimed in claim 11 wherein at least two different probe-binding nucleic acid sequences are linked to the spliceable nucleic acid.

13. The test system as claimed in claim 1 wherein the nucleic acid according to (a) is bound to the solid phase directly covalently or indirectly via a structural element and a binding partner of the structural element or by means of hybridization.

14. The test system as claimed in claim 13 wherein the direct covalent binding is carried out via the vicinal 2',3'-hydroxyl group of the ribose backbone of the nucleic acid.

15. The test system as claimed in claim 13 wherein the structural element is a biotin linker or a dicarboxylic acid linker.

16. The test system as claimed in claim 13 wherein the binding partner is theophylline, xanthine, an aminoglycoside or a nucleic acid-binding protein.

17. The test system as claimed in claim 16 wherein the aminoglycoside is tobramycin.

18. The test system as claimed in claim 16 wherein the nucleic acid-binding protein is IBP.

19. The test system as claimed in claim 1, wherein the solid phase is selected from the group consisting of ceramics, metal, glass and plastic.

20. The nucleic acid as claimed in claim 1, wherein at least one nucleic acid is an RNA.

21. The test system as claimed in claim 20, wherein the RNA is that can be obtained by transcription of a nucleic acid selected from the group consisting of

```
T CTTGGATCGG AAACCCGTCG GCCTCCGAAC GGTAAGAGCC TAGCATGTAG

AACTGGTTAC CTGCAGCCCA AGCTTGCTGC ACGTCTAGGG CGCAGTAGTC

CAGGGTTTCC TTGATGATGT CATACTTATC CTGTCCCTTT TTTTTCCACA

GCTCGCGGTT GAGGACAAAC TCTTCGCGGT CTTTCCAGTG GGGATCCAAG

TGATACCAGC ATCGTCTTGA TGCCCTTGGC AGCACTTGGA TCC (SEQ ID NO:14),

CACT CTTGGATCGG AAACCCGTCG GCCTCCGAAC GGTAAGAGCC TAGCATGTAG

AACTGGTTAC CTGCAGCCCA AGCTTGCTGC ACGTCTAGGG CGCAGTAGTC

CAGGGTTTCC TTGATGATGT CATACTTATC CTGTCCCTTT TTTTTCCACA
```

GCTCGCGGTT GAGGACAAAC TCTTCGCGGT CTTTCCAGTG GGGATCGGCT

TAGTATAGCG AGGTTTAGCT ACACTCGTGC TGAGCCGGAT CC (SEQ ID NO:15),

CACT CTTGGATCGG AAACCCGTCG GCCTCCGAAC GGTAAGAGCC TAGCATGTAG

AACTGGTTAC CTGCAAAGTG ATACCAGCAT CGTCTTGATG CCCTTGGCAG

CACTTCTGCA GCCCAAGCTT GCTGCACGTC TAGGGCGCAG TAGTCCAGGG

TTTCCTTGAT GATGTCATAC TTATCCTGTC CCTTTTTTTT CCACAGCTCG

CGGTTGAGGA CAAACTCTTC GCGGTCTTTC CAGTGGGGAT CC (SEQ ID NO:16),

CCACT CTTGGATCGG AAACCCGTCG GCCTCCGAAC GGTAAGAGCC TAGCATGTAG

AACTGGTTAC CTGCAGGCTT AGTATAGCGA GGTTTAGCTA CACTCGTGCT

GAGCCCTGCA GCCCAAGCTT GCTGCACGTC TAGGGCGCAG TAGTCCAGGG

TTTCCTTGAT GATGTCATAC TTATCCTGTC CCTTTTTTTT CCACAGCTCG

CGGTTGAGGA CAAACTCTTC GCGGTCTTTC CAGTGGGGAT CC (SEQ ID NO:17),

AAGT GATACCAGCA TCGTCTTGAT GCCCTTGGCA GCACTTGAAT TCGAGCTCGC

CCACTCTTGG ATCGGAAACC CGTCGGCCTC CGAACGGTAA GAGCCTAGCA

TGTAGAACTG GTTACCTGCA GCCCAAGCTT GCTGCACGTC TAGGGCGCAG

TAGTCCAGGG TTTCCTTGAT GATGTCATAC TTATCCTGTC CCTTTTTTT

CCACAGCTCG CGGTTGAGGA CAAACTCTTC GCGGTCTTTC CAGTGGGGAT CC (SEQ ID NO:18),

GGCT TAGTATAGCG AGGTTTAGCT ACACTCGTGC TGAGCCGAAT TCGAGCTCGC

CCACTCTTGG ATCGGAAACC CGTCGGCCTC CGAACGGTAA GAGCCTAGCA

TGTAGAACTG GTTACCTGCA GCCCAAGCTT GCTGCACGTC TAGGGCGCAG

TAGTCCAGGG TTTCCTTGAT GATGTCATAC TTATCCTGTC CCTTTTTTT

CCACAGCTCG CGGTTGAGGA CAAACTCTTC GCGGTCTTTC CAGTGGGGAT CC (SEQ ID NO:19), (Th)/To)-5'-linked to a sequence of the formula

CCGCGGTGGC GGCCGCTCTA GAACTAGTGG ATCCGTCGAC TGACTTCAGT

ATGTAATATA CCCCAAACAT TTTACCCACA AAAACCAGG ATTTGAAACT

ATAGCATCTA AAAGTCTTAG GTACTAGAGT TTTCATTTCG GAGCAGGCTT

TTTGAAAAAT TTAATTCAAC CATTGCAGCA GCTTTTGACT AACACATTCT

ACAGTAGGAT CATTTCTATA GGAATCGTCA CTCTTTGACT CTTCAAAGA

GCCACTGAAT CCAACTTGGT TGATGAGTCC CATAACCTTT GTACCCCAGA

GTGAGAAACC GAAATTGAAT CTAAATTAGC TTGGTCCGCA ATCCTTAGCG

TTCGGCCATC TATAATTTTG AATAAAAATT TTGCTTTGCC GTTGCATTTG

TAGTTTTTTC CTTTGGAAGT AATTACAATA TTTTATGGCG CGATGATTCT

TGACCCATCC TATGTACTTC TTTTTTGAAG GGATAGGGCT CTATGGGTGG

GTACAAATGG CAGTCTGACA AGTT (SEQ ID NO:20),

TCCGTCGACT GACTTCAGTA TGTAATATAC CCCAAACATT TTACCCACAA AAACCA-

3' (SEQ ID NO:21)-(Th/To)

CCAGGATTTG AAACTATAGC ATCTAAAAGT CTTAGGTACT AGAGTTTTCA

TTTCGGAGCA GGCTTTTTGA AAAATTTAAT TCAACCATTG CAGCAGCTTT

-continued

```
TGACTAACAC ATTCTACAGT AGGATCATTT CTATAGGAAT CGTCACTCTT

TGACTCTTCA AAAGAGCCAC TGAATCCAAC TTGGTTGATG AGTCCCATAA

CCTTTGTACC CCAGAGTGAG AAACCGAAAT TGAATCTAAA TTAGCTTGGT

CCGCAATCCT TAGCGTTCGG CCATCTATAA TTTTGAATAA AAATTTTGCT

TTGCCGTTGC ATTTGTAGTT TTTTCCTTTG GAAGTAATTA CAATATTTTA

TGGCGCGATG ATTCTTGACC CATCCTATGT ACTTCTTTTT TGAAGGGATA

GGGCTCTATG GGTGGGTACA AATGGCAGTC TGACAAGTT (SEQ ID NO:22),

GTCGACTGAC TTCAGTATGT AATATACCCC AAACATTTTA CCCACAAAAA

ACCAGGATTT GAAACTATAG CATCTAAAAG TCTTAGGTAC TAGAGTTTTC

ATTTCGGAGC AGGCTTTTTG AAAAATTTAA TTCAACCATT GCAGCAGCTT

TTGACTAACA CATTCTACAG TAGGATCATT TCTATAGGAA TCGTCACTCT

TTGACTCTTC AAAAGAGCCA CTGAATCCAA CTTGGTTGAT GAGTCCCATA

ACCTTTGTAC CCCAGAGTGA GAAACCGAAA TTGAATCTAA ATTAGCTTGG

TCCGCAATCC TTAGCGTTCG GCCATCTATA ATTTTGAATA AAAATTTTGC

TTTGCCGTTG CATTTGTAGT TTTTTCCTTT GGAAGTAATT ACAATATTTT

ATGGCGCGAT GATTCTTGAC CCATCCTATG TACTTCTTTT TTGAAGGGAT

AGGGCTCTAT GGGTGGGTAC AAATGGCAGT CTGACAAGTT (SEQ ID NO:23)-3'-(Th/To)

CACTCTTGGA TCGGAAACCC GTCGGCCTCC GAACGGTAAG AGCCTAGCAT

GTAGAACTGG TTACCTGCAG CCCAAGCTTG CTGCACGTCT AGGGCGCAGT

AGTCCAGGGT TTCCTTGATG ATGTCATACT TATCCTGTCC CTTTITTTTC

CACAGCTCGC GGTTGAGGAC AAACTCTTCG CGGTCTTTCC AGTGGGGATC

GGGGATCCTG CTTCAACAGT GCTTGGACGG ATCCTCTAGAC (SEQ ID NO:24) and

TCCGTCGACT GACTTCAGTA TGTAATATAC CCCAAACATT TTACCCACAA

AAAACCAGGA TTTGAAACTA TAGCATCTAA AAGTCTTAGG TACTAGAGTT

TTCATTTCGG AGCAGGCTTT TTGAAAAATT TAATTCAACC ATTGCAGCAG

CTTTTGACTA ACACATTCTA CAGTAGGATC ATTTCTATAG GAATCGTCAC

TCTTTGACTC TTCAAAAGAG CCACTGAATC CAACTTGGTT GATGAGTCCC

ATAACCTTTG TACCCCAGAG TGAGAAACCG AAATTGAATC TAAATTAGCT

TGGTCCGCAA TCCTTAGCGT TCGGCCATCT ATAATTTTGA ATAAAAATTT

TGCTTTGCCG TTGCATTTGT AGTTTTTTCC TTTGGAAGTA ATTACAATAT

TTTATGGCGC GATGATTCTT GACCCATCCT ATGTACTTCT TTTTTGAAGG

GATAGGGCTC TATGGGTGGG TACAAATGGC AGTCTGACA AGTTGGGGATC

CTGCTTCAAC AGTGCTTGGA CGGATCCTCT AGAC (SEQ ID NO:25), where (Th/To) is a sequence selected from

AAGTGATACC AGCATCGTCT TGATGCCCTT GGCAGCACTT GAATT (Th; SEQ ID NO:26), or

GGCTTAGTAT AGCGAGGTTT AGCTACACTC GTGCTGAGCC GAATT (To;

SEQ ID NO:27).
``` where (Th/To) is a sequence selected from
AAGTGATACC AGCATCGTCT TGATGCCCTT GGCAGCACTT GAATT (Th; SEQ ID NO:26), or GGCTTAGTAT AGCGAGGTTT AGCTACACTC GTGCTGAGCC GAATT (To; SEQ ID NO:27).

22. The test system as claimed in claim 1 wherein the composition according to feature (b) comprise small nuclear ribonucleoprotein particle (snRNP) components and non-snRNP components.

23. The test system as claimed in claim 22 wherein the snRNP components comprise U 1, U2, U4, U5 or U6 proteins.

24. The test system as claimed in claim 1 wherein the composition according to feature (b) is a cell extract.

25. The test system as claimed in claim 24 wherein the cell extract is a eucaryotic cell extract or a nuclear extract.

26. The test system as claimed in claim 25 wherein the nuclear extract is obtained from animal cells or from fungal cells.

27. The test system as claimed in claim 26, wherein the animal cells are mammalian cells.

28. The test system as claimed in claim 26, wherein the fungal cells are yeast cells.

29. The test system as claimed in claim 1 additionally comprising a buffer solution, stabilizers or ATP.

30. A method for preparing a test system as claimed in claim 1 which comprises the steps of combining
   (a) one or more identical or different nucleic acid(s), encompassing at least one spliceable nucleic acid, wherein the nucleic acid(s) are immobilized on a solid phase,
   (b) at least one composition comprising splicing components,
   (c) at least one suitable detection probe, and
   (d) at least one device for detecting binding of the detection probe, wherein the device does not comprise a gel.

31. The test system as claimed in claim 1 wherein the device according to feature (d) is an ELISA reader or a device for detecting radioactivity.

32. An RNA that can be obtained by transcription of a nucleic acid selected from the group consisting of

```
T CTTGGATCGG AAACCCGTCG GCCTCCGAAC GGTAAGAGCC TAGCATGTAG

AACTGGTTAC CTGCAGCCCA AGCTTGCTGC ACGTCTAGGG CGCAGTAGTC

CAGGGTTTCC TTGATGATGT CATACTTATC CTGTCCCTTT TTTTTCCACA

GCTCGCGGTT GAGGACAAAC TCTTCGCGGT CTTTCCAGTG GGGATCCAAG

TGATACCAGC ATCGTCTTGA TGCCCTTGGC AGCACTTGGA TCC (SEQ ID NO:14),

CACT CTTGGATCGG AAACCCGTCG GCCTCCGAAC GGTAAGAGCC TAGCATGTAG

AACTGGTTAC CTGCAGCCCA AGCTTGCTGC ACGTCTAGGG CGCAGTAGTC

CAGGGTTTCC TTGATGATGT CATACTTATC CTGTCCCTTT TTTTTCCACA

GCTCGCGGTT GAGGACAAAC TCTTCGCGGT CTTTCCAGTG GGGATCGGCT

TAGTATAGCG AGGTTTAGCT ACACTCGTGC TGAGCCGGAT CC (SEQ ID NO:15),

CACT CTTGGATCGG AAACCCGTCG GCCTCCGAAC GGTAAGAGCC TAGCATGTAG

AACTGGTTAC CTGCAAAGTG ATACCAGCAT CGTCTTGATG CCCTTGGCAG

CACTTCTGCA GCCCAAGCTT GCTGCACGTC TAGGGCGCAG TAGTCCAGGG

TTTCCTTGAT GATGTCATAC TTATCCTGTC CCTTTTTTTT CCACAGCTCG

CGGTTGAGGA CAAACTCTTC GCGGTCTTTC CAGTGGGGAT CC (SEQ ID NO:16),

CCACT CTTGGATCGG AAACCCGTCG GCCTCCGAAC GGTAAGAGCC TAGCATGTAG

AACTGGTTAC CTGCAGGCTT AGTATAGCGA GGTTTAGCTA CACTCGTGCT

GAGCCCTGCA GCCCAAGCTT GCTGCACGTC TAGGGCGCAG TAGTCCAGGG

TTTCCTTGAT GATGTCATAC TTATCCTGTC CCTTTTTTTT CCACAGCTCG

CGGTTGAGGA CAAACTCTTC GCGGTCTTTC CAGTGGGGAT CC (SEQ ID NO:17),

AAGT GATACCAGCA TCGTCTTGAT GCCCTTGGCA GCACTTGAAT TCGAGCTCGC

CCACTCTTGG ATCGGAAACC CGTCGGCCTC CGAACGGTAA GAGCCTAGCA

TGTAGAACTG GTTACCTGCA GCCCAAGCTT GCTGCACGTC TAGGGCGCAG

TAGTCCAGGG TTTCCTTGAT GATGTCATAC TTATCCTGTC CCTTTTTTTT

CCACAGCTCG CGGTTGAGGA CAAACTCTTC GCGGTCTTTC CAGTGGGGAT CC

SEQ ID NO: 18),

GGCT TAGTATAGCG AGGTTTAGCT ACACTCGTGC TGAGCCGAAT TCGAGCTCGC
```

-continued

```
CCACTCTTGG ATCGGAAACC CGTCGGCCTC CGAACGGTAA GAGCCTAGCA
TGTAGAACTG GTTACCTGCA GCCCAAGCTT GCTGCACGTC TAGGGCGCAG
TAGTCCAGGG TTTCCTTGAT GATGTCATAC TTATCCTGTC CCTTTTTTTT
CCACAGCTCG CGGTTGAGGA CAAACTCTTC GCGGTCTTTC CAGTGGGGAT CC
```
(SEQ ID NO:19), (Th)/To)-5'-linked to a sequence of the formula

```
CCGCGGTGGC GGCCGCTCTA GAACTAGTGG ATCCGTCGAC TGACTTCAGT
ATGTAATATA CCCCAAACAT TTTACCCACA AAAAACCAGG ATTTGAAACT
ATAGCATCTA AAAGTCTTAG GTACTAGAGT TTTCATTTCG GAGCAGGCTT
TTTGAAAAAT TTAATTCAAC CATTGCAGCA GCTTTTGACT AACACATTCT
ACAGTAGGAT CATTTCTATA GGAATCGTCA CTCTTTGACT CTTCAAAAGA
GCCACTGAAT CCAACTTGGT TGATGAGTCC CATAACCTTT GTACCCCAGA
GTGAGAAACC GAAATTGAAT CTAAATTAGC TTGGTCCGCA ATCCTTAGCG
TTCGGCCATC TATAATTTTG AATAAAAATT TTGCTTTGCC GTTGCATTTG
TAGTTTTTTC CTTTGGAAGT AATTACAATA TTTTATGGCG CGATGATTCT
TGACCCATCC TATGTACTTC TTTTTTGAAG GGATAGGGCT CTATGGGTGG
GTACAAATGG CAGTCTGACA AGTT (SEQ ID NO:20),
TCCGTCGACT GACTTCAGTA TGTAATATAC CCCAAACATT TTACCCACAA AAAACCA-
3' (SEQ ID NO:21)-(Th/To)
CCAGGATTTG AAACTATAGC ATCTAAAAGT CTTAGGTACT AGAGTTTTCA
TTTCGGAGCA GGCTTTTTGA AAAATTTAAT TCAACCATTG CAGCAGCTTT
TGACTAACAC ATTCTACAGT AGGATCATTT CTATAGGAAT CGTCACTCTT
TGACTCTTCA AAAGAGCCAC TGAATCCAAC TTGGTTGATG AGTCCCATAA
CCTTTGTACC CCAGAGTGAG AAACCGAAAT TGAATCTAAA TTAGCTTGGT
CCGCAATCCT TAGCGTTCGG CCATCTATAA TTTTGAATAA AAATTTTGCT
TTGCCGTTGC ATTTGTAGTT TTTTCCTTTG AAGTAATTA CAATATTTTA
TGGCGCGATG ATTCTTGACC CATCCTATGT ACTTCTTTTT TGAAGGGATA
GGGCTCTATG GGTGGGTACA AATGGCAGTC TGACAAGTT (SEQ ID NO:22),
GTCGACTGAC TTCAGTATGT AATATACCCC AAACATTTTA CCCACAAAAA
ACCAGGATTT GAAACTATAG CATCTAAAAG TCTTAGGTAC TAGAGTTTTC
ATTTCGGAGC AGGCTTTTTG AAAAATTTAA TTCAACCATT GCAGCAGCTT
TTGACTAACA CATTCTACAG TAGGATCATT TCTATAGGAA TCGTCACTCT
TTGACTCTTC AAAAGAGCCA CTGAATCCAA CTTGGTTGAT GAGTCCCATA
ACCTTTGTAC CCCAGAGTGA GAAACCGAAA TTGAATCTAA ATTAGCTTGG
TCCGCAATCC TTAGCGTTCG GCCATCTATA ATTTTGAATA AAAATTTTGC
TTTGCCGTTG CATTTGTAGT TTTTTCCTTT GGAAGTAATT ACAATATTTT
ATGGCGCGAT GATTCTTGAC CCATCCTATG TACTTCTTTT TGAAGGGAT
AGGGCTCTAT GGGTGGGTAC AAATGGCAGT CTGACAAGTT-3' (SEQ ID NO:23)-(Th/To)
CACTCTTGGA TCGGAAACCC GTCGGCCTCC GAACGGTAAG AGCCTAGCAT
GTAGAACTGG TTACCTGCAG CCCAAGCTTG CTGCACGTCT AGGGCGCAGT
```

-continued

```
AGTCCAGGGT TTCCTTGATG ATGTCATACT TATCCTGTCC CTTTTTTTTC

CACAGCTCGC GGTTGAGGAC AAACTCTTCG CGGTCTTTCC AGTGGGGATC

GGGGATCCTG CTTCAACAGT GCTTGGACGG ATCCTCTAGAC (SEQ ID NO:24) and

TCCGTCGACT GACTTCAGTA TGTAATATAC CCCAAACATT TTACCCACAA

AAAACCAGGA TTTGAAACTA TAGCATCTAA AAGTCTTAGG TACTAGAGTT

TTCATTTCGG AGCAGGCTTT TTGAAAAATT TAATTCAACC ATTGCAGCAG

CTTTTGACTA ACACATTCTA CAGTAGGATC ATTTCTATAG GAATCGTCAC

TCTTTGACTC TTCAAAAGAG CCACTGAATC CAACTTGGTT GATGAGTCCC

ATAACCTTTG TACCCAGAG TGAGAAACCG AAATTGAATC TAAATTAGCT

TGGTCCGCAA TCCTTAGCGT TCGGCCATCT ATAATTTTGA ATAAAAATTT

TGCTTTGCCG TTGCATTTGT AGTTTTTTCC TTTGGAAGTA ATTACAATAT

TTTATGGCGC GATGATTCTT GACCCATCCT ATGTACTTCT TTTTTGAAGG

GATAGGGCTC TATGGGTGGG TACAAATGGC AGTCTGACA AGTTGGGGATC
```

CTGCTTCAAC AGTGCTTGGA CGGATCCTCT AGAC (SEQ ID NO:25), where (Th/To) is a sequence selected from AAGTGATACC AGCATCGTCT TGATGCCCTT GGCAGCACTT GAATT (Th, SEQ ID NO:26), and GGCTTAGTAT AGCGAGGTTT AGCTACACTCGTGCTGAGCC GAATT (To, SEQ ID NO:27).

* * * * *